US011311498B2

(12) United States Patent
Guy et al.

(10) Patent No.: US 11,311,498 B2
(45) Date of Patent: Apr. 26, 2022

(54) USE OF CANNABINOIDS IN THE TREATMENT OF EPILEPSY

(71) Applicant: GW Pharma Limited, Cambridge (GB)

(72) Inventors: Geoffrey Guy, Cambridge (GB); Stephen Wright, Cambridge (GB); Orrin Devinsky, New York, NY (US)

(73) Assignee: GW Research Limited, Cambridge (GB)

( * ) Notice: Subject to any disclaimer, the term of this patent is extended or adjusted under 35 U.S.C. 154(b) by 0 days.

(21) Appl. No.: 14/741,829

(22) Filed: Jun. 17, 2015

(65) Prior Publication Data
US 2015/0359756 A1 Dec. 17, 2015

(30) Foreign Application Priority Data

Jun. 17, 2014 (GB) .................................. 1410771

(51) Int. Cl.
A61K 31/05 (2006.01)
A61K 31/352 (2006.01)
A61K 31/19 (2006.01)
A61K 31/5513 (2006.01)
A61K 31/195 (2006.01)
A61K 31/20 (2006.01)
A61K 31/27 (2006.01)
A61K 31/4015 (2006.01)
A61K 31/4166 (2006.01)
A61K 31/423 (2006.01)
A61K 31/496 (2006.01)
A61K 31/53 (2006.01)
A61K 31/551 (2006.01)
A61K 31/5517 (2006.01)
A61K 31/7048 (2006.01)
A61K 36/185 (2006.01)
A61K 45/06 (2006.01)
A61K 31/165 (2006.01)
A61K 31/197 (2006.01)
A61K 31/35 (2006.01)
A61K 31/36 (2006.01)
A61K 47/10 (2017.01)
A61K 47/26 (2006.01)
A61K 47/44 (2017.01)
A61K 9/00 (2006.01)
A61K 9/08 (2006.01)
A61K 31/444 (2006.01)
A61K 31/515 (2006.01)
A61K 31/55 (2006.01)

(52) U.S. Cl.
CPC ............ A61K 31/05 (2013.01); A61K 9/0053 (2013.01); A61K 9/08 (2013.01); A61K 31/165 (2013.01); A61K 31/19 (2013.01); A61K 31/195 (2013.01); A61K 31/197 (2013.01); A61K 31/20 (2013.01); A61K 31/27 (2013.01); A61K 31/35 (2013.01); A61K 31/352 (2013.01); A61K 31/36 (2013.01); A61K 31/4015 (2013.01); A61K 31/4166 (2013.01); A61K 31/423 (2013.01); A61K 31/444 (2013.01); A61K 31/496 (2013.01); A61K 31/515 (2013.01); A61K 31/53 (2013.01); A61K 31/55 (2013.01); A61K 31/551 (2013.01); A61K 31/5513 (2013.01); A61K 31/5517 (2013.01); A61K 31/7048 (2013.01); A61K 36/185 (2013.01); A61K 45/06 (2013.01); A61K 47/10 (2013.01); A61K 47/26 (2013.01); A61K 47/44 (2013.01)

(58) Field of Classification Search
CPC ...... A61K 31/05; A61K 31/052; A61K 31/19; A61K 31/5513
See application file for complete search history.

(56) References Cited

U.S. PATENT DOCUMENTS

| 6,403,126 B1 | 6/2002 | Webster |
| 6,949,582 B1 | 9/2005 | Wallace |
| 8,293,786 B2 | 10/2012 | Stinchcomb |
| 8,673,368 B2 | 3/2014 | Guy et al. |
| 9,017,737 B2 | 4/2015 | Kikuchi et al. |
| 9,023,322 B2 * | 5/2015 | Van Damme ........ A61K 9/0058 424/48 |
| 9,066,920 B2 | 6/2015 | Whalley et al. |

(Continued)

FOREIGN PATENT DOCUMENTS

| CA | 2737447 | 10/2012 |
| CA | 2859934 | 3/2016 |

(Continued)

OTHER PUBLICATIONS

Gresham et al. Neuropsychiatric Disease and Treatment, 2010, vol. 6, pp. 639-645.*
Shukla, R. New Automated Puriifcation Strategies for Scale-up, 2017, pp. 1-5.*
Statement of Opposition for EP10734541.5 mailed Dec. 5, 2014.
[No Author Listed] Orphan Drug Designation Granted for Epidiolex in Dravet syndrome by the FDA—Seven Expanded Access INDs granted by FDA to US physicians to treat with Epidiolex 125 children suffering from intractable epilepsy syndromes. GW Pharmaceuticals Press Release dated Nov. 14, 2013.

(Continued)

Primary Examiner — Samira J Jean-Louis
(74) Attorney, Agent, or Firm — Cooley LLP

(57) ABSTRACT

The present disclosure relates to the use of cannabidiol (CBD) in the treatment of absence seizures. In particular, the disclosure relates to the use of CBD for reducing absence seizures in patients suffering with etiologies that include: Lennox-Gastaut Syndrome; Tuberous Sclerosis Complex; Dravet Syndrome; Doose Syndrome; CDKL5; Dup15q; Jeavons syndrome; Myoclonic Absence Epilepsy; Neuronal ceroid lipofuscinoses (NCL) and brain abnormalities. The disclosure further relates to the use of CBD in combination with one or more anti-epileptic drugs (AEDs).

21 Claims, 1 Drawing Sheet

(56) References Cited

U.S. PATENT DOCUMENTS

| | | |
|---|---|---|
| 9,095,554 B2 | 8/2015 | Lewis et al. |
| 9,125,859 B2 | 9/2015 | Whalley et al. |
| 9,168,278 B2 | 10/2015 | Guy et al. |
| 9,259,449 B2 | 2/2016 | Raderman |
| 9,474,726 B2 | 10/2016 | Guy et al. |
| 9,522,123 B2 | 12/2016 | Whalley et al. |
| 9,730,911 B2 | 8/2017 | Verzura et al. |
| 9,949,936 B2 | 4/2018 | Guy et al. |
| 9,949,937 B2 | 4/2018 | Guy et al. |
| 9,956,183 B2 | 5/2018 | Guy et al. |
| 9,956,184 B2 | 5/2018 | Guy et al. |
| 9,956,185 B2 | 5/2018 | Guy et al. |
| 9,956,186 B2 | 5/2018 | Guy et al. |
| 10,111,840 B2 | 10/2018 | Guy et al. |
| 10,137,095 B2 | 11/2018 | Guy et al. |
| 10,603,288 B2 | 3/2020 | Guy et al. |
| 10,709,671 B2 | 7/2020 | Guy et al. |
| 10,709,673 B2 | 7/2020 | Guy et al. |
| 10,709,674 B2 | 7/2020 | Guy et al. |
| 10,849,860 B2 | 12/2020 | Guy et al. |
| 10,925,525 B2 | 2/2021 | Nakaji |
| 10,966,939 B2 | 4/2021 | Guy et al. |
| 2004/0110828 A1 | 6/2004 | Chowdhury et al. |
| 2005/0266108 A1 | 12/2005 | Flockhart et al. |
| 2006/0039959 A1 | 2/2006 | Wessling |
| 2006/0167283 A1* | 7/2006 | Flockhart ............ C07C 37/004 549/390 |
| 2007/0060638 A1 | 3/2007 | Olmstead |
| 2008/0119544 A1 | 5/2008 | Guy et al. |
| 2008/0188461 A1 | 8/2008 | Guan |
| 2009/0264063 A1 | 10/2009 | Tinsley et al. |
| 2009/0306221 A1 | 12/2009 | Guy et al. |
| 2010/0239693 A1 | 9/2010 | Guy et al. |
| 2010/0317729 A1 | 12/2010 | Guy et al. |
| 2011/0028431 A1 | 2/2011 | Zerbe et al. |
| 2011/0038958 A1 | 2/2011 | Kikuchi et al. |
| 2011/0082195 A1 | 4/2011 | Guy et al. |
| 2012/0004251 A1 | 1/2012 | Whalley et al. |
| 2012/0165402 A1 | 6/2012 | Whalley et al. |
| 2012/0183606 A1 | 7/2012 | Bender et al. |
| 2012/0202891 A1 | 8/2012 | Stinchcomb et al. |
| 2012/0270845 A1* | 10/2012 | Bannister ............ A61K 9/08 514/159 |
| 2013/0209483 A1 | 8/2013 | McAllister |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2014/0343044 A1 | 11/2014 | Ceulemens |
| 2015/0111939 A1 | 4/2015 | Gruening et al. |
| 2015/0181924 A1* | 7/2015 | Llamas ............ A24B 15/16 131/275 |
| 2015/0320698 A1 | 11/2015 | Whalley et al. |
| 2015/0335590 A1 | 11/2015 | Whalley et al. |
| 2015/0343071 A1 | 12/2015 | Vangara |
| 2015/0359755 A1 | 12/2015 | Guy et al. |
| 2015/0359756 A1 | 12/2015 | Guy et al. |
| 2016/0166498 A1 | 6/2016 | Anastassov |
| 2016/0166514 A1 | 6/2016 | Guy et al. |
| 2016/0166515 A1 | 6/2016 | Guy et al. |
| 2016/0220529 A1 | 8/2016 | Guy et al. |
| 2017/0007551 A1 | 1/2017 | Guy et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0224634 A1 | 8/2017 | Vangara et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Whalley et al. |
| 2018/0071210 A1 | 3/2018 | Wilkhu et al. |
| 2018/0228751 A1 | 8/2018 | Stott et al. |
| 2018/0338931 A1 | 11/2018 | Guy et al. |
| 2019/0083418 A1 | 3/2019 | Guy et al. |
| 2019/0314296 A1 | 10/2019 | Wright et al. |
| 2019/0321307 A1 | 10/2019 | Guy et al. |
| 2019/0365667 A1 | 12/2019 | Wright et al. |
| 2020/0138738 A1 | 5/2020 | Guy et al. |
| 2020/0179303 A1 | 6/2020 | Guy et al. |
| 2020/0206152 A1 | 7/2020 | Stott et al. |
| 2020/0206153 A1 | 7/2020 | Whalley et al. |
| 2020/0237683 A1 | 7/2020 | Whalley et al. |
| 2020/0297656 A1 | 9/2020 | Guy et al. |
| 2020/0352878 A1 | 11/2020 | Guy et al. |
| 2020/0368179 A1 | 11/2020 | Guy et al. |
| 2021/0015789 A1 | 1/2021 | Guy et al. |
| 2021/0052512 A1 | 2/2021 | Guy et al. |
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |
| 2021/0093581 A1 | 4/2021 | Guy et al. |
| 2021/0145765 A1 | 5/2021 | Guy et al. |
| 2021/0169824 A1 | 6/2021 | Guy et al. |
| 2021/0177773 A1 | 6/2021 | Guy et al. |
| 2021/0196651 A1 | 7/2021 | Guy et al. |

FOREIGN PATENT DOCUMENTS

| | | |
|---|---|---|
| CN | 101040855 | 9/2007 |
| CN | 103110582 | 5/2013 |
| DE | 102012-105063 | 12/2013 |
| EP | 2448637 | 5/2012 |
| EP | 3 157 512 B1 | 5/2018 |
| GB | 2 384 707 A | 8/2003 |
| GB | 2 434 097 A | 7/2007 |
| GB | 2 434 312 A | 7/2007 |
| GB | 2 450 753 A | 1/2009 |
| GB | 2 456 183 A | 7/2009 |
| GB | 2009/11580.9 | 7/2009 |
| GB | 2 471 523 A | 1/2011 |
| GB | 2 478 595 A | 9/2011 |
| GB | 2 479 153 A | 10/2011 |
| GB | 2 471 565 B | 7/2012 |
| GB | 2 478 072 B | 12/2012 |
| GB | 2 478 074 B | 12/2012 |
| GB | 2 492 487 A | 1/2013 |
| GB | 2487712 | 10/2015 |
| GB | 2531282 A | 4/2016 |
| GB | 2539472 A | 12/2016 |
| WO | WO 02/064109 A2 | 8/2002 |
| WO | WO 03/099302 A1 | 12/2003 |
| WO | WO 04/016246 A1 | 2/2004 |
| WO | WO 04/016277 A2 | 2/2004 |
| WO | WO 2006/054057 A2 | 5/2006 |
| WO | WO 2006/133941 A2 | 12/2006 |
| WO | WO 2007/083098 A1 | 7/2007 |
| WO | WO 2007/138322 A1 | 12/2007 |
| WO | WO 2008/019146 | 2/2008 |
| WO | WO 2008/094181 A2 | 8/2008 |
| WO | WO 2008/129258 A1 | 10/2008 |
| WO | WO 2008/144475 | 11/2008 |
| WO | WO 2008/021394 | 12/2008 |
| WO | WO 2008/146006 A1 | 12/2008 |
| WO | WO 2009/007697 A1 | 1/2009 |
| WO | WO 2009/007698 | 1/2009 |
| WO | WO 2009/020666 | 12/2009 |
| WO | WO 2011/001169 A1 | 1/2011 |
| WO | WO 2011/121351 A1 | 10/2011 |
| WO | WO 2012/033478 | 3/2012 |
| WO | WO 2012/093255 A1 | 7/2012 |
| WO | WO 2013/032351 A1 | 3/2013 |
| WO | WO 2015142501 A1 * | 9/2015 ........... A61K 31/685 |
| WO | WO 2015/184127 A2 | 12/2015 |
| WO | WO 2015/193667 | 12/2015 |
| WO | WO 2015/193668 A1 | 12/2015 |
| WO | WO 2016/059405 | 4/2016 |
| WO | WO 2016/084075 | 6/2016 |
| WO | WO 2015/187988 A1 | 7/2016 |

(56) References Cited

FOREIGN PATENT DOCUMENTS

| WO | WO 2016/118391 | 7/2016 |
|---|---|---|
| WO | WO 2016/147186 | 9/2016 |
| WO | WO 2016/022936 | 11/2016 |
| WO | WO 2016/199148 | 12/2016 |
| WO | WO 2017/168138 | 10/2017 |
| WO | WO 2018/002636 | 1/2018 |
| WO | WO 2018/002637 | 1/2018 |
| WO | WO 2018/037203 | 3/2018 |

OTHER PUBLICATIONS

[No Author Listed] Cannabinoid. Wikipedia. Retrieved on Jul. 9, 2015 from https://en.wikipedia.org/wiki/Cannabinoid.
[No Author Listed] Estimating the Maximum Safe Starting Dose in Initial Clinical Trials for Therapeutics in Adult Healthy Volunteers. FDA Guidance for Industry, Jul. 2005.
[No Author Listed] GW Pharmaceuticals Announces Epidiolex Receives Fast Track Designation from FDA for the Treatment of Dravet Syndrome. GW Pharmaceuticals Press Release dated Jun. 6, 2014.
[No Author Listed] GW Pharmaceuticals Announces Physician Reports of Epidiolex Treatment Effect in Children and Young Adults with Treatment-resistant epilepsy from Physician-Led Expanded Access Treatment Program. GW Pharmaceuticals Press Release dated Jun. 17, 2014.
Alger, Not too excited? Thank your endocannabinoids. Neuron. Aug. 17, 2006;51(4):393-5.
Ames et al., Anticonvulsant effect of cannabidiol. S Afr Med J. Jan. 4, 1986;69(1):14.
Arain et al., Pregabalin in the management of partial epilepsy. Neuropsychiatr Dis Treat. 2009;5:407-13. Epub Aug. 20, 2009.
Avoli et al., Cellular and molecular mechanisms of epilepsy in the human brain. Prog Neurobiol. Oct. 2005;77(3):166-200.
Bakhsh, Miftaah-al-Khazaain. 1930: 607-8. Urdu. Exhibit 3.
Bancaud et al., Proposal for Revised Clinical and Electroencephalographic Classification of Epileptic Seizures. Epilepsia. Aug. 1981;22(4):489-501.
Bhatt et al., Indigenous plants in traditional healthcare system in Kedarnath valley of western Himalaya. Indian J Tradit Knowl. Apr. 2008;7(2):300-10.
Bhattacharyya et al., Modulation of mediotemporal and ventrostriatal function in humans by Delta9-tetrahydrocannabinol: a neural basis for the effects of *Cannabis sativa* on learning and psychosis. Arch Gen Psychiatry. Apr. 2009;66(4):442-51. doi:10.1001/archgenpsychiatry.2009.17.
Bostanci et al., The effects of octanol on penicillin induced epileptiform activity in rats: an in vivo study. Epilepsy Res. Oct. 2006;71(2-3):188-94. Epub Jul. 27, 2006.
Brust et al., Marijuana use and the risk of new onset seizures. Trans Am Clin Climatol Assoc. 1992;103:176-81.
Carlini et al., Hypnotic and antiepileptic effects of cannabidiol. J Clin Pharmacol. Aug.-Sep. 1981;21(8-9 Suppl):417S-427S. Medline abstract only.
Consroe et al., Anticonvulsant drug antagonism of delta9tetrahydrocannabinol-induced seizures in rabbits. Res Commun Chem Pathol Pharmacol. Jan. 1977;16(1):1-13.
Consroe et al., Anticonvulsant interaction of cannabidiol and ethosuximide in rats. J Pharm Pharmacol. Aug. 1977;29(8):500-1.
Consroe et al., Anticonvulsant nature of marihuana smoking. JAMA. Oct. 20, 1975;234(3):306-7.
Consroe et al., Cannabidiol—antiepileptic drug comparisons and interactions in experimentally induced seizures in rats. J Pharmacol Exp Ther. Apr. 1977;201(1):26-32.
Consroe et al., Effects of cannabidiol on behavioral seizures caused by convulsant drugs or current in mice. Eur J Pharmacol. Sep. 24, 1982;83(3-4):293-8.
Cortesi et al., Potential therapeutical effects of cannabidiol in children with pharmacoresistant epilepsy. Med Hypotheses. 2007;68(4):920-1. Epub Nov. 16, 2006.

Cunha et al., Chronic administration of cannabidiol to healthy volunteers and epileptic patients. Pharmacology. 1980;21(3):175-85.
Czapinski et al., Randomized 36-month comparative study of valproic acid (VPA), phenytoin (PHT), phenobarbital (PB) and carbamazepine (CBZ) efficacy in patients with newly diagnosed epilepsy with partial complex seizures. J Neurolog Sci. Sep. 1997;150:S162. Abstract only. 2 pages.
Dasa et al., Brhat Nighantu Ratnakara (Saligramanighantubhusanam). vol. IV. 1997:170. Sanskrit. Exhibit 5.
Davis et al., A predominant role for inhibition of the adenylate cyclase/protein kinase A pathway in ERK activation by cannabinoid receptor 1 in N1E-115 neuroblastoma cells. J Biol Chem. Dec. 5, 2003;278(49):48973-80. Epub Sep. 29, 2003.
Davis et al., Antiepileptic action of marijuana-active substances. Federation Proceedings. 1949;8:284-5.
Deshpande et al., Cannabinoid CB1 receptor antagonists cause status epilepticus-like activity in the hippocampal neuronal culture model of acquired epilepsy. Neurosci Lett. Jan. 2007;411(1):11-6. Epub Nov. 15, 2006.
Dravet, The core Dravet syndrome phenotype. Epilepsia. Apr. 2011;52 Suppl 2:3-9. doi: 10.1111/j.1528-1167.2011.02994.x.
Eadie, Shortcomings in the current treatment of epilepsy. Expert Rev Neurother. Dec. 2012;12(12):1419-27. doi: 10.1586/ern.12.129.
Eggers, Temporal lobe epilepsy is a disease of faulty neuronal resonators rather than oscillators, and all seizures are provoked, usually by stress. Med Hypotheses. 2007;69(6):1284-9.
Engel, Report of the ILAE classification core group. Epilepsia. Sep. 2006;47(9):1558-68.
Ferdinand et al., Cannabis—psychosis pathway independent of other types of psychopathology. Schizophr Res. Nov. 15, 2005;79(2-3):289-95. Epub Aug. 25, 2005.
Fisher et al., The impact of epilepsy from the patient's perspective I. Descriptions and subjective perceptions. Epilepsy Res. Aug. 2000;41(1):39-51.
Gabor et al., Lorazepam versus phenobarbital: Candidates for drug of choice for treatment of status epilepticus. J Epilepsy. Jan. 1990;3(1):3-6.
Gastaut, Clinical and electroencephalographical classification of epileptic seizures. Epilepsia. Mar. 1970;11(1):102-13.
Geffrey et al., Cannabidiol (CBD) Treatment for Refractory Epilepsy in Tuberous Sclerosis Complex (TSC). American Epilepsy Society. 2014: Abstract 2.427. Last accessed from https://www.aesnet.org/meetings_events/annual_meeting_abstracts/view/1868979 on Jun. 30, 2015.
Gross et al., Marijuana use and epilepsy: prevalence in patients of a tertiary care epilepsy center. Neurology. Jun. 8, 2004;62(11):2095-7.
Hill et al., $\Delta^9$-Tetrahydrocannabivarin suppresses in vitro epileptiform and in vivo seizure activity in adult rats. Epilepsia. Aug. 2010;51(8):1522-32. doi: 10.1111/j.1528-1167.2010.02523.x. Epub Feb. 26, 2010.
Iuvone et al., Neuroprotective effect of cannabidiol, a non-psychoactive component from *Cannabis sativa*, on beta-amyloid-induced toxicity in PC12 cells. J Neurochem. Apr. 2004;89(1):134-41.
Jeavons et al., Sodium valproate in treatment of epilepsy. Br Med J. Jun. 15, 1974;2(5919):584-6.
Jones et al., Cannabidiol displays antiepileptiform and antiseizure properties in vitro and in vivo. J Pharmacol Exp Ther. Feb. 2010;332(2):569-77. doi: 10.1124/jpet.109.159145. Epub Nov. 11, 2009.
Joy et al., Marijuana and Medicine. Assessing the Science Base. National Academy Press. Washington D.C. 1999. 170 pages.
Karler et al., The cannabinoids as potential antiepileptics. J Clin Pharmacol. Aug.-Sep. 1981;21(8-9 Suppl):437S-447S.
Khan et al., Khazaain-al-Adiva. vol. I. 1911:885. Urdu. Exhibit 7.
Khan et al., Khazaain-al-Adiva. vol. I. 1911:886. Urdu. Exhibit 4.
Khan et al., Khazaain-al-Advia, vol. I. 1911: 889. Urdu. Exhibit 3.
Khan et al., Khazaain-al-Advia, vol. I. 1911: 889. Urdu. Exhibit 4.
Khan et al., Muheet-e-Azam, vol. II. 1887: 147. Persian. Exhibit 1.

(56) References Cited

OTHER PUBLICATIONS

Klitgaard et al., Electrophysiological, neurochemical and regional effects of levetiracetam in the rat pilocarpine model of temporal lobe epilepsy. Seizure. Mar. 2003;12(2):92-100.

Kramer et al., Febrile infection-related epilepsy syndrome (FIRES): pathogenesis, treatment, and outcome: a multicenter study on 77 children. Epilepsia. Nov. 2011;52(11):1956-65. doi:10.1111/j.1528-1167.2011.03250.x. Epub Aug. 29, 2011.

Kwan et al., Definition of drug resistant epilepsy: consensus proposal by the ad hoc Task Force of the ILAE Commission on Therapeutic Strategies. Epilepsia. Jun. 2010;51(6):1069-77. doi:10.1111/j.1528-1167.2009.02397.x. Epub Nov. 3, 2009. Erratum in: Epilepsia. Sep. 2010;51(9):1922.

Long et al., The pharmacological actions of cannabidiol. Drugs of the Future. Jul. 2005;30(7):747-53.

Lutz, On-demand activation of the endocannabinoid system in the control of neuronal excitability and epileptiform seizures. Biochem Pharmacol. Nov. 1, 2004;68(9):1691-8.

Maa et al., The case for medical marijuana in epilepsy. Epilepsia. Jun. 2014;55(6):783-6. doi: 10.1111/epi.12610. Epub May 22, 2014.

Mackie, Cannabinoid receptors as therapeutic targets. Annu Rev Pharmacol Toxicol. 2006;46:101-22.

Majoosi, et al. Kaamil-al-Sena'ah, Part II, Central Council for Research in Unani Medicine. 2005:116. Arabic. Exhibit 2.

McCormick et al., On the cellular and network bases of epileptic seizures. Annu Rev Physiol. 2001;63:815-46.

Mechoulam et al., Toward drugs derived from cannabis. Naturwissenschaften. Apr. 1978;65(4):174-9.

Merlis, Proposal for an international classification of the epilepsies. Epilepsia. Mar. 1970;11(1):114-9.

Ng et al., Illicit drug use and the risk of new-onset seizures. Am J Epidemiol. Jul. 1990;132(1):47-57.

Obay et al., Antiepileptic effects of ghrelin on pentylenetetrazole-induced seizures in rats. Peptides. Jun. 2007;28(6):1214-9. Epub Apr. 19, 2007.

Pereira et al., Study pharmacologic of the GABAergic and glutamatergic drugs on seizures and status epilepticus induced by pilocarpine in adult Wistar rats. Neurosci Lett. Jun. 4, 2007;419(3):253-7. Epub Apr. 13, 2007.

Pertwee, Cannabinoid receptor ligands: clinical and neuropharmacological considerations, relevant to future drug discovery and development. Expert Opin Investig Drugs. Jul. 2000;9(7):1553-71.

Pohl et al., Effects of flunarizine on Metrazol-induced seizures in developing rats. Epilepsy Res. Sep. 1987;1(5):302-5.

Porter et al., Report of a parent survey of cannabidiol-enriched cannabis use in pediatric treatment-resistant epilepsy. Epilepsy Behav. Dec. 2013;29(3):574-7. doi: 10.1016/j.yebeh.2013.08.037.

Press et al., Parental reporting of response to oral cannabis extracts for treatment of refractory epilepsy. Epilepsy Behav. Apr. 2015;45:49-52. doi: 10.1016/j.yebeh.2015.02.043. Epub Apr. 3, 2015.

Rauca et al., The role of superoxide dismutase and alpha-tocopherol in the development of seizures and kindling induced by pentylenetetrazol—influence of the radical scavenger alpha-phenyl-N-tert-butyl nitrone. Brain Res. May 29, 2004;1009(1-2):203-12.

Resstel et al., 5-HT1A receptors are involved in the cannabidiol-induced attenuation of behavioural and cardiovascular responses to acute restraint stress in rats. Br J Pharmacol. Jan. 2009;156(1):181-8.

Sadanandasarma et al., Rasatarangini. 11th Ed. 1979:720-3. Sanskrit. Exhibit 6.

Sander, The epidemiology of epilepsy revisited. Curr Opin Neurol. Apr. 2003; 16(2):165-70.

Sastri et al., Anandakandam. 1st Edition. 1952:241. Sanskrit. Exhibit 2.

Scuderi et al., Cannabidiol in medicine: a review of its therapeutic potential in CNS disorders. Phytother Res. May 2009;23(5):597-602.

Stott et al., Cannabinoids for the pharmaceutical industry. Euphytica. 2004;140:83-93.

Swann et al., The effects of seizures on the connectivity and circuitry of the developing brain. Ment Retard Dev Disabil Res Rev. 2004;10(2):96-100.

Thomas et al., Evidence that the plant cannabinoid Delta9-tetrahydrocannabivarin is a cannabinoid CB1 and CB2 receptor antagonist. Br J Pharmacol. Dec. 2005;146(7):917-26.

Thurman et al., Standards for epidemiologic studies and surveillance of epilepsy. Epilepsia. Sep. 2011;52 Suppl 7:2-26. doi: 10.1111/j.1528-1167.2011.03121.x.

Trembly et al., Double-blind clinical study of cannabidiol as a secondary anticonvulsant. Marijuana '90 International Conference on Cannabis and Cannabinoids. Kolymbari, Crete. Jul. 8-11, 1990.

Usami et al., Synthesis and pharmacological evaluation in mice of halogenated cannabidiol derivatives. Chem Pharm Bull (Tokyo). Nov. 1999;47(11):1641-5.

Vollner et al., Haschisch XX: Cannabidivarin, ein neuer Haschisch-Inhaltsstoff. Tetrahedron Lett. 1969;10(3):145-7.

Wahle et al., Development of tolerance to the anticonvulsant effect of valproate but not to ethosuximide in a rat model of absence epilepsy. Eur J Pharma. May 1990;181(1-2):1-8.

Wallace et al., Assessment of the role of CB1 receptors in cannabinoid anticonvulsant effects. Eur J Pharmacol. Sep. 28, 2001;428(1):51-7.

Weston et al., Tetrahydrocannabivarin exhibits anticonvulsant effects in a piriform cortical brain slice model of epileptiform activity. Pro British Pharm Soc 75th Anniv Meeting. Dec. 31, 2006. Found on: http://www.pA2online.org/abstract/abstract.jsp?abid=28533. Abstract Only. 1 Page.

Wingerchuk, Cannabis for medical purposes: cultivating science, weeding out the fiction. Lancet. Jul. 24-30, 2004;364(9431):315-6.

Yuriev, Endogenic cannabinoid system is a new perspective object of pharmacotherapeutic effect to disease of nervous system, Ukrainsky Metodichny Chasopis, 2005; 6(50): 21-9.

Zuardi et al., Cannabidiol, a *Cannabis sativa* constituent, as an antipsychotic drug. Braz J Med Biol Res. Apr. 2006;39(4):421-9. Epub Apr. 3, 2006.

[No Author Listed] "Cannabidiol for Aicardi Syndrome," *Salutaris.*, Retrieved on Feb. 10, 2017, Retrieved from the internet: URL http://web.archive.org/web20141012220050/http://salutarisdrops.com/cannabidiol-aicardi-syndrome/, © 2014, 3 pages.

[No Author Listed] "Cannabidiol Therapy for Aicardi Syndrome" Aug. 2014, 4 pages.

[No Author Listed] "Convulsive Disorders and Their Interference with Driving," Medicos., Retrieved Feb. 10, 2017, Retrieved from internet: URL https://www.medicosporlaseguridadvial.com/en/clinical-subjects/neurologic-diseases/convulsive-disorders-and-their-interference-with-driving/. 2014, 3 pages.

[No Author Listed] "GW Pharmaceuticals Provides Update on Orphan Program in Childhood Epilepsy for Epidiolex®," *GW Pharm*. Available online Nov. 14, 2013. Retrieved Feb. 10, 2017, Retrieved from the internet: URL http://www.gwpharm.com/GW%20Phannaceuticals%20Provides%20Update%20on%20rphan%20Program%20in%20Childhood%20Epilepsy%20for%20Epidiolex.aspx, 5pages.

[No Author Listed] "GW Pharmaceuticals Receives Orphan Drug Designation by FDA for Epidiolex® in the Treatment of Lennox-Gastaut Syndrome," *GW Pharm.*, Available online Feb. 28, 2014, Retrieved Feb. 10, 2017, Retrieved from the internet: URL https://www.gwpharm.com/about-us/news/gw-pharmaceuticals-receives-orphan-drug-designation-fda-epidiolex%C2%AE-treatmeat-lennox, 4 pages.

[No Author Listed] "What are the Highest CBD Strains?" accessed Feb. 16, 2017, available online at www.leafscience.com, published Oct. 15, 2014, 2 pages.

Booth et al., "Legalization's opening of medical pot research is dream and nightmare," Denver Post, Dec. 14, 2013.

Braida et al., "Post-ischernic treatment with cannabidiol prevents electroencephalographic flattening, hyperlocomotion and neuronal injury in gerbils" *Neuroscience Letters.*, 346:61-64, 2003.

Catherine Jacobson et al: "Survey of Current Cannabidiol Use in Pediatric Treatment-Resistant Epilepsy", Apr. 22, 2013 (Apr. 22,

(56) References Cited

OTHER PUBLICATIONS

2013), XP055238831, Retrieved from the Internet: URL:https://www.thcint.com/uploads/1/9/3/7/19371199/cannabidiol_use_in_pediatric_epilepsy.pdf.
Castel-Branco et al., "The Maximal Electroshock Seizure (MES) Model in the Preclinical Assessment of Potential New Antiepileptic Drugs," *Methods Find Exp Clin Pharmacol.*, 31(2): 101-106, 2009.
Chiu et al., "The Influence of Cannabidiol and Δ9-Tetrahydrocannabinol on Cobalt Epilepsy in Rats," *Epilepsia.*, 20:365-375, 1979.
Combined Search and Examination Report dated Jan. 4, 2012 for Application No. GB1116789.7.
Combined Search and Examination Report dated Mar. 25, 2011 for Application No. GB1100043.7.
Combined Search and Examination Report dated Sep. 5, 2014 for Application No. GB1414813.4.
Combined Search and Examination Report under Sections 17 and 18(3) for International Application No. GB1410771.8, dated Feb. 27, 2015, 7 pages.
Combined Search and Examination Report under Sections 17 and 18(3) for International Application No. GB1418166.3, dated Jul. 2, 2015, 8 pages.
Combined Search and Examination Report under Sections 17 and 18(3) for International Application No. GB1418170.5, dated Jul. 2, 2015, 6 pages.
Combined Search and Examination Report under Sections 17 and 18(3) for International Application No. GB1418171.3, dated Jun. 29, 2015, 8 pages.
Communication of a Notice of Opposition for Application No. 10734541.5, dated Dec. 17, 2014, 1 page.
Communication Pursuant to Article 94(3) EPC in European Patent Application No. 10734541.5, dated Oct. 23, 2012, 3 pages.
Consroe et al., "Therapeutic Potential of Cannabinoids in Neurological Disorders," Chapter 2, pp. 21-49, Cannabinoids as Therapeutic Agents, R. Mechoulam, ed CRC Press, Boca Raton (1986).
Consroe et al., Chapter 12, "Potential Role Cannabinoids for Therapy of Neurological Disorders," p. 459 in Marijuana/Cannabinoids: Neurobiology and Neurophysiology, ed. L. Murphy (1992).
Cortez et al., Chapter 10 "Pharmacologic Models of Generalized Absence Seizures in Rodents," Models Seizures Epilepsy., 111-126, 2006.
Decision in Opposition proceedings (Art. 101(3)(a) and 106(2) EPC in European Patent Application No. EP2448637, dated Dec. 15, 2016, 91 pages.
Declaration of Professor Anthony G. Marson In the Inter Partes Review of U.S. Pat. No. 9,066,920, dated Dec. 13, 2016, 28 pages.
Declaration of Professor Leslie Benet In the Inter Partes Review of U.S. Pat. No. 9,066,920, dated Nov. 22, 2016, 18 pages.
Dreifus et al., "Proposal for Revised Clinical and Electroencephalographic Classification of Epileptic Seizures" *Epilepsie.*, 22:489-501, 1981.
Drugs of the Future, 39(1): 49-56, Jan. 2014 notes Orphan Drug designation for CBD for Lennox-Gastaut Syndrome.
Engel et al., Chapter 1, "What Should be Modeled," In Models Seizure Epilepsy., 2006, 14 pages.
Examination Report dated Mar. 18, 2014 for Application No. GB1100043.7.
Fariello, "Parenteral Penicillin in Rats: An Experimental Model of Multifocal Epilepsy," *Epilepsia*, 17:217-222, 1976.
Gallily et al., "Overcoming the Bell-Shaped Dose-Response of Cannabidiol by Using Cannabis Extract Enriched in Cannabidiol." *Pharmacology & Pharmacy.*, 6:75-85, Jan. 2015.
Gedde, M. et al. Epilepsey Currents 2014 Posters excerpt pp. 449-450.
Green, "CBD: An Unconventional Therapy," available online at http://nugs.com/article/cbd-an-unconventional-therapy.html, published Mar. 24, 2014, 5 pages.
Guimaraes et al., "Antianxiety effect of cannabidiol in the elevated plus-maze," *Psychopharmacology.*, 100:558-559, 1990.

Heinemann et al., "An Overview of In Vitro Seizure Models in Acute and Organotypic Slices" Chapter 4, 35-44, 2006.
Iannotti et al., "Nonpsychotropic plant cannabinoids, cannabidivarin (CBDV) and cannabidiol (CBD), activate and desensitize transient receptor potential vanilloid 1 (TRPV1) channels in vitro: Potential for the treatment of neuronal hyperexcitability," *ACS Chem. Neurosci.*, 5:1131-1141, Jul. 16, 2014.
International Preliminary Repor on Patentability in International Application No. PCT/GB2010/051066, dated May 3, 2011, 6 pages.
International Preliminary Report on Patentability dated Apr. 18, 2017 for Application No. PCT/GB2015/053030.
International Preliminary Report on Patentability dated Dec. 12, 2013 for Application No. PCT/GB2012/052284.
International Preliminary Report on Patentability dated Jun. 9, 2011 for Application No. PCT/GB2010/051066.
International Search Report and Written Opinion dated Dec. 13, 2010 for Application No. PCT/GB2010/051066.
International Search Report and Written Opinion dated May 30, 2011 for Application No. PCT/GB2011/050649.
International Preliminary Report on Patentability in International Application No. PCT/GB2011/051775, dated Oct. 8, 2016.
International Search Report and Written Opinion dated Aug. 26, 2015 for Application No. PCT/GB2015/051775.
International Search Report and Written Opinion dated Nov. 16, 2012 for Application No. PCT/GB2012/052284.
International Search Report in International Application No. PCT/GB2010/051066, dated Nov. 16, 2010, 3 Pages.
International Search Report in International Application No. PCT/GB2012/050002, dated Feb. 24, 2012, pages.
Izzo et al., "Non-psychotropic plant cannabinoids: new therapeutic opportunities from an ancient herb," Trends in Pharmacological Sciences., 30(10):515-527, 2009.
Letter from Opponenet Rregarding Oral Proceedings in European Patent No. EP2448637, dated Oct. 20, 2016, 6 pages.
Lindamood et al., "Effects of Δ9-Tetrahydrocannabinol and Cannabidiol on Sodium-Dependent High Affinity Choline Uptake in the Rat Hippocampus1," *J Pharmacology Experimental Therapeutics.*, 213(2):216-221, 1980.
Malfait et al., "The nonpsychonctive cannabis constituent cannabidiol is an oral anti-arthritic therapeutic in murine collagen-induced arthritis," *PNAS.*, 97(17):9561-9566, Aug. 15, 2000.
Mattson et al. "Comparison of carbamazepine, phenobarbital, phenytoin, and primidone in partial and secondarily generalized tonic-clonic seizures." *N Engl J Med.*, 313(3):145-151, Jul. 18, 1985.
Mattson et al., "Prognosis tor total control of complex partial and secondary generalized tonic clonic seizures," *Neurology.*, 47:68-76, 1996.
Mechoulam et al., "Cannabidiol: An Overview of Some Pharmacological Aspects," J Clin Pharmacol., 42:11S-19S, 2002.
Models of Chemically-Induced Acute Seizures 127-152, 2006.
Morad et at. "Conversion to Sirolimus-Based Immunosuppression in Maintenance Liver Transplantation Patients," *Liver Transplantation.*, 13:658-664, 2007.
Notice of Allowance in Applicatian No. U.S. Appl. No. 13/380,305, dated Dec. 10, 2014, 5 pages.
Notice of Allowance in U.S. Appl. No. 13/380,305, dated Mar. 19, 2015, 7 pages.
Notice of Appeal in European Patent No. EP2448637, dated Feb. 14, 2017, 5 pages.
Notice of Opposition to a European Patent No. EP2448637, dated Dec. 5, 2014, 20 pages.
Office Action in U.S. Appl. No. 13/380,305, dated Aug. 25, 2014.
Opponent Response to the Preliminary Opinion of the Opposition Division in European Patent No. EP2448637, dated Jun. 23, 2016, 27 pages.
Opponent Response to the Preliminary Opinion of the Opposition Division in European Patent No. EP2448637, dated Sep. 9, 2016, 25 pages.
Opponent Response to the Written Submissions in European Patent No. EP2448637, dated Oct. 12, 2016, 18 pages.
Opponent Response to the Written Submissions in European Patent No. EP2448637, dated Oct. 20, 2016, 3 pages.

(56) References Cited

OTHER PUBLICATIONS

Opponent Written Submission in European Patent No. EP2448637, dated Nov. 4, 2016, 3 pages.
Pelliccia et al., "Treatment with CBD in oily solution of drug-resistant paediatric epilepsies," Available online Sep. 2, 2010, Retrieved Jun. 30, 2015, Retrieved from the internet: URL http://www.cannabismed.org/studies/ww_en_db_study_show.php?s_id=173&&search_pattern=EPILEPSY, 2 pages, Abstract only.
Pertwee, "The diverse CB1 and CB2 receptor pharmacology of three plant cannabinoids: Δ9-tetrahydrocannabinol, cannabidiol and Δ9-tetrahydrocannabivarin," Br. J. Pharmacol., 153(2):199-215, 2008.
Pertwee, Chapter 3, "The Pharmacology and Therapeutic Potential of Cannabidiol," pp. 32-83 in the book Neuroscience Intelligence Unit: Cannabinoids, Ed Vincenzo Di Marzo, Springer Science & Business Media, (2004).
Petition for Inter Panes Review of U.S. Pat. No. 9,066,920, dated Dec. 16, 2016, 77 pages.
Reply of the Patent Proprietor to the Notice(s) of Opposition in European Patent No. 2448637, dated May 28, 2015, 12 pages.
Reply to Communication from the Examining Division in European Patent Application No. 10734541.5, dated Feb. 15, 2013, 54 pages.
Reply to EPO Communication in European Patent No. EP2448637, dated Nov. 2, 2016, 45 pages.
Reply to Opponent's Written Submission in European Patent No. EP2448637, dated Nov. 4, 2016 13 pages.
Reply to Opponent's Written Submissions in European Patent No. EP2448637, dated Oct. 18, 2016, 5 pages.
Reply to Preliminary Opinion and Opponent's Observations in European Patent No. EP2448637, dated Sep. 9, 2016, 65 pages.
Request for Continued Examination with the Amendment and Information Disclosure Statement in U.S. Appl. No. 13/380,305, filed Mar. 2, 2015, 3 pages.
Rubio et al., "In Vivo Experimental Models of Epilepsy," Central Nervous System Agents in Medicinal Chemistry., 10:298-309, 2010.
Third Party Observations for Application No. AU2012314128 mailed Mar. 19, 2015.
Third Party Observations for Application No. EP1 1712658.1 mailed Nov. 22, 2013.
Third Preliminary Amendment under 37 C.F.R. 1.115 in U.S. Appl. No. 13/380,305, dated May 23, 2014, 4 pages.
"Turkanis et al., ""An Electrophysiological Analysis of the Anticonvulsant Action of Cannabidiol on Limbic Seizures in Conscious Rats,"" Epilepsia., 20:351-363, 1979".
Velisek., "Models of Chemically-Induced Acute Seizures," *Models Seizure Epilepsy.*, 127-152, 2006.
Veliskova., Chapter 48 "Behavioral Characterization of Seizures in Rates," *Models Seizures Epilepsy.*, 601-611, 2006.
Whole-Plant Cannabinoids Outperform Single Molecule Compounds at 1/5, Charlotte's Web: By the Stanley Brothers (Jan. 11, 2017) available at https://www.cwhemp.com/blog/whole-plant-cw-hemp-cannabinoids.
Written Opinion of the International Application No. PCT/GB2010/0051066, dated Nov. 22, 2010, 4 pages.
Zhao et al., Chapter 27 "Repetitive Seizures in the Immature Brain," Models Seizures Epilepsy., 341-350, 2006.
Zuardi et al., "Cannabidiol: from an inactive cannabinoid to a drag with wide spectrum of action," Rev Bras Psiquiatr., 30(3): 271-80 (2008).
U.S. Appl. No. 15/346,844, filed Nov. 9, 2016, Whalley et al.
U.S. Appl. No. 13/977,766, filed Jul. 1, 2013, Whalley et al.
U.S. Appl. No. 14/345,968, filed Mar. 20, 2014, Whalley et al.
U.S. Appl. No. 15/284,766, filed Oct. 4, 2016, Guy et al.
U.S. Appl. No. 15/449,084, filed Mar. 3, 2017, Guy et al.
U.S. Appl. No. 15/449,124, filed Mar. 3, 2017, Guy et al.
U.S. Appl. No. 15/449,185, filed Mar. 3, 2017, Guy et al.
U.S. Appl. No. 15/449,204, filed Mar. 3, 2017, Guy et al.
U.S. Appl. No. 15/449,177, filed Mar. 3, 2017, Guy et al.
U.S. Appl. No. 14/881,954, filed Oct. 13, 2015, Guy et al.
U.S. Appl. No. 14/881,969, filed Oct. 13, 2015, Guy et al.
U.S. Appl. No. 15/449,402, filed Mar. 3, 2017, Guy et al.
U.S. Appl. No. 15/449,535, filed Mar. 3, 2017, Guy et al.
U.S. Appl. No. 14/741,829, filed Jun. 17, 2015, Guy et al.
U.S. Appl. No. 15/183,947, filed Jun. 16, 2016, Guy et al.
U.S. Appl. No. 15/519,233, filed Apr. 14, 2017, Guy et al.
U.S. Appl. No. 15/519,244, filed Apr. 14, 2017, Guy et al.
Annex to the Communication-Opposition for Application No. 10734541.5, dated Jan. 28, 2016, 5 pages.
Chiron, C. et al. Epilepsia, 2011, vol. 52 Suppl. 2, pp. 72-75.
Cunha et al., "Chronic Administration of Cannabidiol to Healthy Volunteers and Epileptic Patients," Pharmacology., 21(3):175-185 (1980).
Devinsky et al., Cannabidiol: Pharmacology and potential therapeutic role in epilepsy and other neuropsychiatric disorders, 2014 Epilepsia, 55(6), 791-802.
International Preliminary Report on Patentability dated Sep. 1, 2017 for Application No. PCT/GB2016/051792.
Russo, Taming THC: potential cannabis synergy and phytocannabinoid-terpenoid entourage effects, 163 British J. of Pharm. 1344-1364 (2011).
Silva, R. et al., Can. J. Neurol. Sci. 2006 vol. 33 pp. 783-786.
Supplemental Expert Statement of Professor Benjamin J. Whalley, dated Nov. 4, 2016, 9 pages.
Expert Statement of Vincenzo Di Marzo for Application No. EP10734541.5, dated Sep. 9, 2016.
Expert Statement of Professor Benjamin J. Whalley for Application No. EP10734541.5, dated Sep. 9, 2016.
Expert Statement of Professor Anthony G Marson for Application No. EP10734541.5.
Expert Statement of Dr. Emma Louise Cheetham, dated Nov. 4, 2016, 6 pages.
Third Party Observations for Application No. EP10734541.5 mailed Apr. 3, 2017.
Holmes et al. "Choosing the Correct AED: From Animal Studies to the Clinic," Pediatr Neurol. Mar. 2008; 38(3): 151-162.
Statement of Grounds of Appeal for Eurpoean Application No. 10734541.5 in the name of GW Pharma and Otsuka Pharmaceutical Co. Limited Appellant/Opponent: lnsys Therapeutics Inc., dated Apr. 21, 2017.
Statement of Grounds of Appeal for Eurpoean Application No. 10734541.5 on behalf of the Proprietors: GW Pharma Limited and Otsuka Pharmaceutical CO Limited, dated Apr. 12, 2017.
Patent Owners' Preliminary Response for IPR2017-00503 dated Apr. 11, 2017, 45 pages.
Decision in IPR2017-00503 dated Jul. 7, 2017, 26 pages.
Mares et al., Electrical Stimulation-Induced Models of Seizures in Model of Seizures and Epilepsy (Asla Pitkänen, Philip A. Schwartzkroin & Solomon L. Moshé, eds.), 2004.
Petrocellis et al., "Effects of cannabinoids and cannabinoid-enriched Cannabis extracts on TRP channels and endocannabinoid metabolic enzymes," British Journal of Pharmacology (2011) 163 1479-1494.
ElSohly and Gul, Chapter 1, Handbook of Cannabis, ed. Roger G. Pertwee, pp. 3-22 (2014).
Etienne de Meijer, Chapter 5, Handbook of Cannabis, ed. Roger G. Pertwee, pp. 89-110 (2014).
David J. Potter, Chapter 4, Handbook of Cannabis, ed. Roger G. Pertwee, pp. 65-88 (2014).
Utah Controlled Substances Advisory Committee Meeting, Nov. 12, 2013, available at https://www.utah.gov/pmn/files/81459.pdf.
"When to Expect Results from CW Hemp Oil", downloaded Sep. 5, 2017, https://www.cwhemp.com/blog/expecting-results-from-hemp.
C.C. de Oliveira, et al., "Anticonvulsant activity of β-caryophyllene against pentylenetetrazol-induced seizures," Epilepsy Behav. Mar. 2016, 56:26-31.
Neto, et al., "The role of polar phytocomplexes on anticonvulsant effects of leaf extracts of Lippia Alba (Mill.) N.E. Brown chemotypes," *J. Pharm Pharmacol*. 61(7):933-9 (2009).
Crespel, et al., "Lennox-Gastaut Syndrome," Chapter 14, in Epileptic Syndromes in Infancy, Childhood, and Adolescence, 5th Edition, ed. M. Bureau, et al., pp. 189-216.
A. Wallace, et al., Pediatr. Drugs, 18:197-208 (2016).

(56) References Cited

OTHER PUBLICATIONS

M.M. Gedde, "Clinical Experience with Cannabis in Treatment-Resistant Pediatric Epilepsy," http://www.theroc.us/images/gedde_presentation.pdf, Sep. 9-11, 2014.
E.C. Rosenberg, et al., Neurotherapeutics, 12(4): 747-768 (2015).
B.C. Kahan, et al., Trials, 16: 405 (2015).
Lieu et al., "Assessment of self-selection bias in a pediatric unilateral hearing loss study," *Otolaryngol Head Neck Surg.* 142(3): 427-433 (2010).
Bipolar Health Group (Charlotte's Web Hemp Remedy, available online at http:/bipolarhealthgroup.org/index.php/charlottes-web-hemp-remedy/, accessed Sep. 6, 2017.
Thurstone (Avoid Charlotte's Web for Epilepsy, available online at http://drthurstone.com/charlotted-web-not-safest-option-epiliepsy-treatment/, published Jun. 26, 2014.
Martin, A.R. NIDS research monograph, (1987) vol. 79, pp. 48-58.
Manno, "Status Epilepticus: Current Treatment Strategies," The Neurohospitalist. Jan. 2011, 1(1):23-31.
FDA, "Warning Letters and Test Results for Cannabidiol-Related Products," 2015 Warning Letters Retrieved from: https://www.fda.gov/newsevents/publichealthfocus/ucm484109.htm.
FDA, "Warning Letters and Test Results for Cannabidiol-Related Products," 2016 Warning Letters Retrieved from: https://www.fda.gov/newsevents/publichealthfocus/ucm484109.htm.
Dulac, "Use of Lamotrigine in Lennox-Gastaut and Related Epilepsy Syndromes," J. Child Neurol., 12(Supplement 1), S23-S29 (1997).
Dulac, "Vigabatrin in Childhood Epilepsy," J. Child Neurolog., 6(Supplement 2), S30-S37 (1991).
IUPHAR/BPS Guide to Pharmacology, Entry for Δ9-tetrahydrocannabidiol, available at http://www.guidetopharmacology.org/GRAC/LigandDisplayForward?tab=biology&ligandId=2424.
Marinol Label Retrieved from: https://www.accessdata.fda.gov/drugsatfda_docs/label/2006/018651s025s026lbl.pdf.
Guerrini et al., "Lamotrigine and Seizure Aggravation in Severe Myoclonic Epilepsy," Epilepsia, 39(5):508-512, 1998.
Miller et al., "Mapping genetic modifiers of survival in a mouse model of Dravet syndrome," Genes, Brain and Behavior (2014) 13: 163-172.
Stafstrom et al., "Models of Pediatric Epilepsies: Strategies and Opportunities," Epilepsia, vol. 47, No. 8, 2006.
Yu et al., "Reduced sodium current in GABAergic interneurons in a mouse model of severe myoclonic epilepsy in infancy," Nature Neuroscience vol. 9 No. 9 Sep. 2006 pp. 1142-1149.
Van Rijckevorsel, Neuropsychiatr Dis Treat. Dec. 2008; 4(6): 1001-1019.
Brown et al., Child Neurology Foundation, "LGS" (Lennox-Gastaut Syndrome), available at http://www.childneurologyfoundation.org/disorders/lgs-lennox-gastaut-syndrome.
Löscher W, Schmidt D. "Modern antiepileptic drug development has failed to deliver: ways out of the current dilemma." Epilepsia. Apr. 1, 2011, 52(4):657-78.
Bertram, "The Relevance of Kindling for Human Epilepsy," Apr. 1, 2007, 48(s2):65-74.
Klitgaard H, Matagne A, Gobert J, Wülfert E. "Evidence for a unique profile of levetiracetam in rodent models of seizures and epilepsy." European journal of pharmacology. Jul. 24, 1998, 353(2):191-206.
Declaration of Professor H. Steve White In the Inter Partes Review of U.S. Pat. No. 9,066,920, dated Oct. 24, 2017, 69 pages.
[No Author Listed], Cover and Table of Contents, J Pharmacology and Exp Therapeutics, Feb. 2010, 332(2), 4 pages.
American Epilepsy Society, Three Studies Shed New Light on the Effectiveness of Cannabis in Epilepsy, Oct. 14, 2014, 2 pages.
Arslan and Tirnaksiz, "Self-emulsifying Drug Delivery Systems," FABAD J Pharm Sci, 2013,38(1): 55-64.
Arzimanoglou et al., "All children who experience epileptic falls do no necessarily have Lennox-Gastaut syndrome . . . but many do," Epileptic Discord, 2011, 13:S3-S13.
Barker-Haliski et al., "How Clinical Development Can, and Should. Inform Translational Science," Neuron, Nov. 2014, 84: 582-593.
Corny et al., "Clobazam in the treatment of Lennox-Gastaut syndrome," Epilepsia, May 2009, 50(5): 1158-1166.
EPO Reply to Proprietor's Statement of Grounds of Appeal in European Patent No. EP2448637, dated Sep. 8, 2017, 5 pages.
EPO Response to the Statement of Grounds of Appeal in European Patent No. 2448637, dated Sep. 5, 2017, 17 pages.
Gardner [online], "Comes Now Epidiolex (FDA Approves IND Studies of CBD)," BeyondTHC.com, Oct. 22, 2013, retrieved on Jan. 31, 2018, URL <http://www.beyondthc.com/comes-now-epidiolex-fda-approves-ind-studies-of-cbd>, 4 pages.
GB Combined Search and Examination Report in Application No. GB1611544.6, dated Mar. 29, 2017, 8 pages.
GB Combined Search and Examination Report in GB Appln. No. GB1514079.1, dated May 4, 2016, 9 pages.
GWPharm [online], "GW Pharmaceuticals Announces Preliminary Results of Phase 2a Study for its Pipeline Compound GWP42006," GW Pharmaceuticals Press Release, Feb. 21, 2018, retrieved on Jun. 29, 2018, URL <https://www.gwpharm.com/about-us/news/gw-pharmaceuticals-announces-preliminary-results-phase-2a-study-its-pipeline-compound>, 5 pages.
Hill, "Cannabidivarin-rich cannabis extracts are anticonvulsant in mouse and rat via a CB1 receptor-independent mechanism," British Journal of Pharmacology, Oct. 2013, 170(3): 679-692.
ICE Epilepsy Alliance, The Dravet Syndrome Spectmm, Nov. 2008, 2 pages.
*Insys Development Company, Inc.* v. *GW Pharma Limited and Otsuka Pharmaceutical Co., Ltd.*, Declaration by Mark Polyakov, IPR2017-00503, U.S. Pat. No. 9,066,920, dated May 29, 2018, 1 page.
*Insys Development Company, Inc.* v. *GW Pharma Limited and Otsuka Pharmaceutical Co., Ltd.*, Deposition of H. Steve White, dated Dec. 13, 2016, 50 pages.
*Insys Development Company, Inc.* v. *GW Pharma Limited and Otsuka Pharmaceutical Co., Ltd.*, Petitioner's Brief Regarding Ground III of the IPR, IPR2017-00503, U.S. Pat. No. 9,066,920, dated May 29, 2018, 45 pages.
*Insys Development Company, Inc.* v. *GW Pharma Limited and Otsuka Pharmaceutical Co., Ltd.*, Petitioner's Reply to Patent Owner's Response, IPR2017-00503, U.S. Pat. No. 9,066,920, dated Jun. 19, 2018, 6 pages.
*Insys Development Company, Inc.* v. *GW Pharma Limited and Otsuka Pharmaceutical Co., Ltd.*, Petitioner's Reply to Response in IPR2017-00503, U.S. Pat. No. 9,066,920, dated Jan. 19, 2018, 36 pages.
Jones et al. [online], Info & Metrics / Article Information,"Cannabidiol Displays Antiepileptiform and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info, 9 pages.
Kaplan, "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-marajuana.html>, 3 pages.
Kelley et al., "Doose syndrome (myoclonic-astatic epilepsy): 40 years of progress," Developmental Medicine & Child Neurology, Aug. 2010, 52: 988-993.
Lewis, "Mystery Mechanisms," TheScientist.com, Jul. 29, 2016, retrieved on Nov. 8, 2017, URL <https://www.the-scientist.com/?articles.view/articleNo/46688/title/Mystery-Mechanisms/>, 2 pages.
Manni et al., "Obstructive Sleep Apnea in a Clinical Series of Adult Epilepsy Patients: Frequency and Features of the Comorbidity," Epilepsia, Jun. 2003, 44(6): 836-840.
McNamara, "Chapter 19: Pharmacotherapy of the Epilepsies,", Goodman & Gilman's The Pharmacological Basis of Therapeutics 11th ed., McGraw-Hill Companies, 2006, 501-525.
Oakley et al., "Dravet Syndrome Insights into pathophysiology and therapy from a mouse model of Dravet syndrome," Epilepsia, Apr. 2011, 52(Suppl. 2): 59-61.
PCT International Preliminary Report on Patentability in International Appln. No. PCT/GB2015/051775, dated Aug. 10, 2016, 9 pages.

(56) References Cited

OTHER PUBLICATIONS

PCT International Search Report and Written Opinion in International Appln. No. PCT/US2017/050868, dated Aug. 6, 2017, 14 pages.
PCT International Search Report and Written Opinion in International Appln. PCT/GB2017/051943, dated Sep. 12, 2017, 10 pages.
Poortman-van der Meer, "A contribution to the improvement of accuracy in the quantitation of THC," Forensic Science International, Apr. 1999, 101(1): 1-8.
Porter et al., "Randomized, multicenter, dose-ranging trial of retigabine for partial-onset seizures," Neurology, Apr. 2007, 68(15): 1197-1204.
Pouton, "Lipid formulations for oral administration of drugs: non-emulsifying, self-emulsifying and 'self-microemulsifying' drug delivery systems, "Eur. J Pharm Sci, Oct. 2000, 11(Supp. 2): S93-S98.
Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.
Ramantani et al., "Epilepsy in Aicardi—Goutieres syndrome," Official J Eur Paediatric Neurology Society, 2014, 18: 30-37.
Sperling et al., "Carisbamate as adjunctive treatment of partial onset seizures in adults in two randomized, placebo-controlled trials," Epilepsia, Mar. 2010, 51(3):333-343.
Stephenson, "In Memoriam: Professor Jean Aicardi (1926-2015)," Pediatric Neurology, Jan. 2016, 54: 3-4.
Thumma et al., "Influence of plasticizers on the stability and release of a prodrug of Δ9-tetrahydrocannabinol incorporated in poly (ethylene oxide) matrices," Eur J Pharmceutics and Biopharmaceutics, Oct. 2008, 70(2): 605-614.
USPTO Information Disclosure Statement Form PTO-1449 in U.S. Appl. No. 13/380,305, dated Nov. 24, 2014, 8 pages.
Zhornitsky and Potvin, "Cannabidiol in Humans—The Quest for Therapeutic Targets," Pharmaceuticals, 2012, 5:529-552.
[No Author Listed], "Missouri House passes cannabis extract legislation," Kansas City Star, 2014, https://kansascity.com/news/politics-government/article346747.html, 2 pages.
Banerjee et al., "Case Report: Aicardi syndrome: A report of five Indian cases," Neurology India, Mar. 2006, 54(1): 91-93.
cdc.gov [online], "2 to 20 years: Girls Stature-for-age and Weigh-for-age percentiles," National Center for Health Statistics and National Center for Chronic Disease Prevention and Health Promotion, last modified Nov. 2000, <https://www.cdc.gov/growthcharts/data/set1clinical/cj411022,pdl>, 1 page.
Chou, "Theoretical basis, experimental design, and computerized simulation of synergism and antagonism in drug combination studies," Pharmacol Rev., Sep. 2006, 58(3), 621-681.
GB Combined Search and Examination Report in GB Appln. No. GB1605448.8, dated Jan. 12, 2017, 6 pages.
*Insys Development Company, Inc.* v. *GW Pharma Limited and Otsuka Pharmaceutical Co., Ltd.*, Final Written Decision in IPR2017-00503, U.S. Pat. No. 9,066,920, dated Jan. 3, 2019, 40 pages.
Kuhn et al., "Potent activity of carfilzomib, a novel, irreversible inhibitor of the ubiquitin-proteasome pathway, against preclinical models of multiple myeloma," Blood, Nov. 2007, 110(9): 3281-3290.
Leo et al., "Cannabidiol and epilepsy: Rationale and therapeutic potential," Pharamacological Research, Mar. 2016, 107: 85-92.
Morelli et al., "The effects of cannabidiol and its synergism with bortezomib in multiple myeloma cell lines. A role for transient receptor potential Vanilloid type-2," Int J Cancer, Jun. 2014, 134(11): 2534-2546.
MyVirtualMedicalCentre [online], "Aicardi syndrome," mvmc.com, Feb. 2004, retrieved on Jan. 25, 2019, https://www.myvmc.com/diseases/aicardi-syndrome/, 6 pages.
Nabissi et al., "Cannabinoids synergize with cafilzomib, reducing multiple myeloma cells viability and migration," Oncotarget, Oct. 2016, 7: 77553.

PCT International Preliminary Report on Patentability in International Appln. No. PCT/GB2017/052229, dated Feb. 26, 2019, 7 pages.
PCT International Search Report and Written Opinion in International Appln. No. PCT/GB2017/051913, dated Sep. 15, 2017, 9 pages.
PCT International Search Report and Written Opinion in International Appln. No. PCT/GB2017/051914, dated Sep. 12, 2017, 10 pages.
PCT International Search Report and Written Opinion in International Appln. No. PCT/GB2017/052229, dated Oct. 6, 2017, 10 pages.
Pruitt et al., "Ethanol in Liquid Preparations Intended for Children," Padiatrics, Mar. 1984: 73(3): 405-407.
Raab et al., "Multiple myeloma," Lancet, Jul. 2009, 374(9686): 324-339.
Rosenkrantz et al., "Oral and Parenteral Formulations of Marijuana Constituents," J Pharm Sci, Jul. 1972, 61(7)1106-1112.
Strickley, "Solubilizing Excipients in Oral and Injectable Formulations," Table VIII, Pharmaceutical Research, Feb. 2004, 21(2): 201-230.
Velasco et al., "Anticancer mechanisms of cannabinoids," Curr Oncol, Mar. 2016, 23(2): S23-S32.
U.S. Appl. No. 13/380,305, filed Mar. 19, 2012, Benjamin Whalley.
U.S. Appl. No. 14/579,061, filed Dec. 22, 2014, Benjamin Whalley.
U.S. Appl. No. 15/346,844, filed Nov. 9, 2016, Benjamin Whalley.
U.S. Appl. No. 16/149,983, filed Oct. 2, 2018, Benjamin Whalley.
U.S. Appl. No. 13/977,766, filed Jul. 1, 2013, Benjamin Whalley.
U.S. Appl. No. 14/345,968, filed Mar. 20, 2014, Benjamin Whalley.
U.S. Appl. No. 14/741,783, filed Jun. 17, 2015, Geoffrey Guy.
U.S. Appl. No. 15/284,766, filed Oct. 4, 2016, Geoffrey Guy.
U.S. Appl. No. 15/449,084, filed Mar. 3, 2017, Geoffrey Guy.
U.S. Appl. No. 15/449,124, filed Mar. 3, 2017, Geoffrey Guy.
U.S. Appl. No. 15/449,185, filed Mar. 3, 2017, Geoffrey Guy.
U.S. Appl. No. 15/449,204, filed Mar. 3, 2017, Geoffrey Guy.
U.S. Appl. No. 15/449,177, filed Mar. 3, 2017, Geoffrey Guy.
U.S. Appl. No. 15/948,412, filed Apr. 9, 2018, Geoffrey Guy.
U.S. Appl. No. 14/881,954, filed Oct. 13, 2015, Geoffrey Guy.
U.S. Appl. No. 14/881,969, filed Oct. 13, 2015, Geoffrey Guy.
U.S. Appl. No. 15/449,402, filed Mar. 3, 2017, Geoffrey Guy.
U.S. Appl. No.15/449,535, filed Mar. 3, 2017, Geoffrey Guy.
U.S. Appl. No. 16/198,141, filed Nov. 21, 2018, Geoffrey Guy.
U.S. Appl. No. 15/183,947, filed Jun. 16, 2015, Geoffrey Guy.
U.S. Appl. No. 15/519,233, filed Apr. 14, 2017, Geoffrey Guy.
U.S. Appl. No. 15/519,244, filed Apr. 14, 2017, Geoffrey Guy.
U.S. Appl. No.15/640,033, filed Jun. 30, 2017, Jitinder Wilkhu.
U.S. Appl. No. 15/751,563, filed Feb. 9, 2018, Colin Stott.
U.S. Appl. No.16/090,039, filed Sep. 28, 2018, Geoffrey Guy.
U.S. Appl. No. 16/314,583, filed Dec. 31, 2018, Stephen Wright.
U.S. Appl. No. 16/314,569, filed Dec. 31, 2018, Harshit Shah.
U.S. Appl. No. 16/328,209, filed Feb. 25, 2019, Colin Stott.
Notice of Opposition to European Patent Application No. EP15784111.5, Patent No. EP3206716, dated May 10, 2021.
[Anonymous], "GW Pharma—GW Pharmaceuticals Announces New Physician Reports of Epidiolex® Treatment Effect in Children and Young Adults With Treatment-Resistant Epilepsy," Oct. 14, 2014; https://ir.gwpharm.com/news-releases/news-release-details/gw-pharmaceuticals-announces-new-physician-reports-epidiolexr-0, 4 pages.
[Anonymous], "Salutaris Drops Buy Salutaris Drops—Salutaris Drops," Oct. 12, 2014; http://web.archive.org/web/20141012130255/http://salutarisdrops.com/buy-salutaris-drops/, 2 pages.
[Anonymous], "GW Pharma Initiates Second Phase 3 Pivotal Study of Epidiolex® (CBD) in Lennox-Gastaut Syndrome," Jun. 11, 2015; https://www.benzinga.com/pressreleases/18/11/g12748407/gw-pharmaceuticals-announces-second-positive-phase-3-pivotal-trial-for, 5 pages.
[No Author Listed],"ILAE Proposal for Revised Terminology for Organization of Seizures and Epilepsies," 2010, 2 pages.
AAN 67th Annual Meeting Abstract, Apr. 2015; https://www.aan.com/PressRoom/Home/GetDigitalAsset/11570, 1 page.

(56) References Cited

OTHER PUBLICATIONS

Babayeva et al., "Marijuana Compounds: A Non-Conventional Therapeutic Approach to Epilepsy in Children," J. Addict. Neuropharmacol, 1:1 (2014); doi:10.24966/AAD-7276/100002, 9 pages.

Camfield, "Definition and natural history of Lennox-Gastaut Syndrome," Epilepsia, 52:3-9 (2011).

Campos-Castello, "Rational approach to treatment options for Lennox-Gastaut syndrome," Orphanet, Mar. 2003; https://www.orpha.net/data/patho/GB/uk-Lennox.pdf, 5 pages.

Ciccone, "Drop Seizure Frequency in Lennox-Gastaut Decrease With Cannabidiol," Neurology Advisor, Apr. 26, 2017; retrieved from the Internet: URL:https://neurologyadvisor.com/aan-2017-coverage/aan-2017-cannabidiol-reduces-drop-seizures-in-lennox-gasaut-syndrome/article/652931.

Citti et al., "Pharmaceutical and biomedical analysis of cannabinoids: A critical review," Journal of Biopharmaceutical and Biomedical Analysis, 147:565-579 (2018).

Devinsky et al., "Epidiolex (Cannabidiol) in Treatment Resistant Epilepsy," Apr. 2015; https://epilepsyontario.org/wp-content/uploads/2015/Epidiolex-Cannabidiol-in-Treatment-Resistant-Epilepsy AAN-POSTER 08Apr2015.pdf, 1 page.

Devinsky et al., "Efficacy and safety of Epidiolex (cannabidiol) in children and young adults with treatment-resistant epilepsy: Initial data from expanded access program," Jan. 2015.

Devinsky et al., "Cannabidiol in patients with treatment-resistant epilepsy: an open-label interventional trial," Lancet Neurology, 15(3):270-278 (2015).

Devinsky et al., "Cannabidiol (CBD) significantly reduces drop seizure frequency in Lennox-Gastaut syndrome (LGS): results of a dose-ranging, multi-center, randomized, double-blind, placebo-controlled trial (GWPCARE3)," Epilepsia, 58:S13-S14 (2017).

Devinsky et al., "Trial of Cannabidiol for Drug-Resistant Seizures in the Dravet Syndrome," N Engl J Med, 376(21):2011-2020 (2017).

Gedde, Retrospective Case Review of High CBD, Low THC Cannabis Extract (Realm Oil) for Intractable Seizure Disorders, 2013 Realm of Caring Foundation, 4 pages.

Geffrey et al., "Drug-drug interaction between clobazam and cannabidiol in children with refractory epilepsy," Epilepsia, 56(8):1246-1251 (2015).

Hess et al., "Cannabidiol as a new treatment for drug-resistant epilepsy in tuberous sclerosis complex," Epilepsia, 57(10):1617-1624 (2016).

Montouris, "Rational approach to treatment options for Lennox-Gastaut syndrome," Epilepsia, 52:10-20 (2011).

Perucca, "Cannabinoids in the Treatment of Epilepsy: Hard Evidence at Last?" Journal of Epilepsy Research, 7(2):61-76 (2017).

Pertwee, "The Pharmacology and Therapeutic Potential of Cannabidiol," Cannabinoids, Chapter 3, DiMarzo, V. (Ed.), pp. 32-83 (2004).

Screenshot confirming date of Epidiolex (Cannabidiol) in Treatment Resistant Epilepsy, Apr. 2015; https://epilepsyontario.org/wp-content/uploads/2015/Epidiolex-Cannabidiol-in-Treatment-Resistant-Epilepsy AAN-POSTER 08Apr2015.pdf, 1 page.

Smith, R. M., "Identification of Butyl Cannabinoids in Marijuana," Journal of Forensic Sciences, 42:610-618 (1997).

Study NCT02224690—A Study to Investigate the Efficacy and Safety of Cannabidiol (*GWP42003-P; CBD*) AS Adjunctive Treatment for Seizures Associated With Lennox-Gastaut Syndrome in Children and Adults, Aug. 22, 2014; https://clinicaltrials.gov/ct2/show/NCT02224690, 1 page.

Van Straten et al., "Update on the Management of Lennox-Gastaut Syndrome," Pediatric Neurology, 47:153-161 (2012).

Williams, "The Key to Healing Broken Bones May be Found in This Illegal Drug," Jul. 25, 2015; https://www.fool.com/investing/high-growth/2015/07/25/the-key-to-healing-broken-bones-may-be-found-in-th.aspx#:~:text=As%20published%20in%20the%20Journal,rats%20in%20just%20eight%20 weeks, 5 pages.

Wright et al., Cannabidiol (CBD) in Dravet Syndrome: A Randomised, Dose-Ranging Pharmacokinetics and Safety Trial (GWPCARE1), Epilepsia, 58(Suppl. 5):S5-S199 (2017), p. 0240 Abstract, 1 page.

Russo et al., "Upholding WAG/Rij Rats as a Model of Absence Epileptogenesis: Hidden Mechanisms and a New Theory on Seizure Development," Neuroscience and Biobehavioral Reviews, 71 (2016) 388-408.

Russo et al., "Pharmacology of Epileptogenesis and Related Comorbidities in the WAG/Rij Rat Model of Genetic Absence Epilepsy," Journal of Neuroscience Methods, 310 (2018) 54-62.

Sarkisova et al., "The WAG/Rij Strain: A Genetic Animal Model of Absence Epilepsy with Comorbidity of Depression," Progress in Neuro-Psychopharmacology & Biological Psychiatry, 35 (2011) 854-876.

Leo et al., "Cognitive impairment in the WAG/Rij rat absence model is secondary to absence seizures and depressive-like behavior," Progress in Neuropsychopharmacology & Biological Psychiatry, 94 (2019) 109652.

Leo et al., "Antiepileptogenic effects of Ethosuximide and Levetiracetam in WAG/Rij rats are only temporary," Pharmacological Reports, 71 (2019) 833-838.

\* cited by examiner

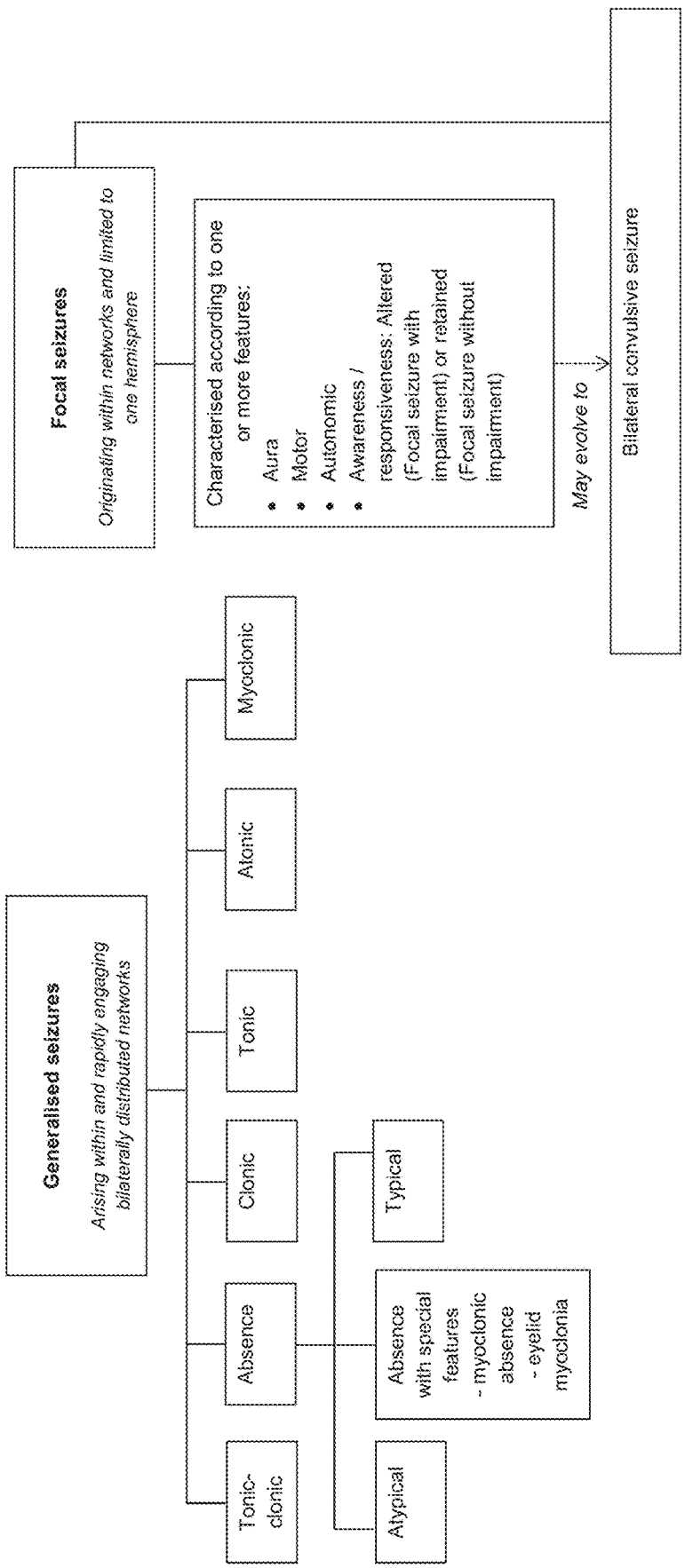

USE OF CANNABINOIDS IN THE TREATMENT OF EPILEPSY

CROSS REFERENCE TO RELATED APPLICATION

This application claims priority to U.K. Application Number 1410771.8, filed Jun. 17, 2014, the disclosures of which are hereby incorporated by reference herein in its entirety.

FIELD OF THE INVENTION

The present invention relates to the use of cannabidiol (CBD) in the treatment of absence seizures. In one embodiment the patients suffering from absence seizures are children and young adults. CBD appears particularly effective in reducing absence seizures in patients suffering with etiologies that include: Lennox-Gastaut Syndrome; Tuberous Sclerosis Complex; Dravet Syndrome; Doose Syndrome; CDKL5; Dup15q; Jeavons syndrome; Myoclonic Absence Epilepsy; Neuronal ceroid lipofuscinoses (NCL) and brain abnormalities in comparison to other seizure types.

Significantly CBD proved very effective in treating a sub-type of absence seizures, namely myoclonic absence seizures. The etiologies of patients which suffer from myoclonic absence seizures include Doose Syndrome, Jeavons syndrome and Myoclonic Absence Epilepsy syndrome.

In these patients treatment with CBD reduced the occurrence of absence seizures or myoclonic absence seizures by greater than 50% in a large proportion of patients, 64% and 75% respectively. This was surprising given that the proportion of patients benefiting from a greater than 50% reduction in total seizures was significantly less, (46%), in all subjects treated.

Preferably the CBD used is in the form of a highly purified extract of *cannabis* such that the CBD is present at greater than 98% of the total extract (w/w) and the other components of the extract are characterised. In particular the cannabinoid tetrahydrocannabinol (THC) has been substantially removed, to a level of not more than 0.15% (w/w) and the propyl analogue of CBD, cannabidivarin, (CBDV) is present in amounts of up to 1%. Alternatively, the CBD may be a synthetically produced CBD.

In use the CBD may be used concomitantly with one or more other anti-epileptic drugs (AED). When used in combination with another AED the CBD may be formulated for administration separately, sequentially or simultaneously with the one or more AED or the combination may be provided in a single dosage form. Where the CBD is formulated for administration separately, sequentially or simultaneously it may be provided as a kit or together with instructions to administer the one or more components in the manner indicated. It may also be used as the sole medication, i.e. as a monotherapy.

BACKGROUND TO THE INVENTION

Epilepsy occurs in approximately 1% of the population worldwide, (Thurman et al., 2011) of which 70% are able to adequately control their symptoms with the available existing anti-epileptic drugs (AED). However, 30% of this patient group, (Eadie et al., 2012), are unable to obtain seizure freedom from the AED that are available and as such are termed as suffering from intractable or "treatment-resistant epilepsy" (TRE).

Intractable or treatment-resistant epilepsy was defined in 2009 by the International League Against Epilepsy (ILAE) as "failure of adequate trials of two tolerated and appropriately chosen and used AED schedules (whether as monotherapies or in combination) to achieve sustained seizure freedom" (Kwan et al., 2009).

Individuals who develop epilepsy during the first few years of life are often difficult to treat and as such are often termed treatment-resistant. Children who undergo frequent seizures in childhood are often left with neurological damage which can cause cognitive, behavioral and motor delays.

Childhood epilepsy is a relatively common neurological disorder in children and young adults with a prevalence of approximately 700 per 100,000. This is twice the number of epileptic adults per population.

When a child or young adult presents with a seizure, investigations are normally undertaken in order to investigate the cause. Childhood epilepsy can be caused by many different syndromes and genetic mutations and as such diagnosis for these children may take some time.

The main symptom of epilepsy is repeated seizures. In order to determine the type of epilepsy or the epileptic syndrome that a patient is suffering from, an investigation into the type of seizures that the patient is experiencing is undertaken. Clinical observations and electroencephalography (EEG) tests are conducted and the type(s) of seizures are classified according to the ILAE classification described below and in FIG. 1.

The International classification of seizure types proposed by the ILAE was adopted in 1981 and a revised proposal was published by the ILAE in 2010 and has not yet superseded the 1981 classification. FIG. 1 is adapted from the 2010 proposal for revised terminology and includes the proposed changes to replace the terminology of partial with focal. In addition the term "simple partial seizure" has been replaced by the term "focal seizure where awareness/responsiveness is not impaired" and the term "complex partial seizure" has been replaced by the term "focal seizure where awareness/consciousness is impaired".

From FIG. 1 it can be seen that Generalised seizures, where the seizure arises within and rapidly engages bilaterally distributed networks, can be split into six subtypes: Tonic-Clonic (grand mal) seizures; Absence (petit mal) Seizures; Clonic Seizures; Tonic Seizures; Atonic Seizures and Myoclonic Seizures.

Focal (partial) seizures where the seizure originates within networks limited to only one hemisphere, are also split into sub-categories. Here the seizure is characterized according to one or more features of the seizure, including aura, motor, autonomic and awareness/responsiveness. Where a seizure begins as a localized seizure and rapidly evolves to be distributed within bilateral networks this seizure is known as a Bilateral convulsive seizure, which is the proposed terminology to replace Secondary Generalised Seizures (generalized seizures that have evolved from focal seizures and are no longer remain localized).

Absence seizures can occur as Typical absence seizures; Atypical absence seizures or Absence seizures with special features such as Myoclonic absence and Eyelid myoclonia.

Typical absence seizures are generalized seizures with a sudden onset and offset of altered awareness. The altered awareness can vary in severity dependent on the specific syndrome that the patient is suffering from. Clonic move ments of the eyelids, head, eyebrows, chin perioral or other facial parts can occur, whereas myoclonus of limbs only occurs rarely. In addition, absence status epilepticus can also occur.

Atypical absence seizures have a less sudden onset and offset of loss of awareness than occurs in typical absence seizures. They are associates with other features such as loss of muscle tone of the head, trunk or limbs and subtle myoclonic jerks. A loss of awareness is usually minimal.

Myoclonic absence seizures present with bilateral rhythmic myoclonic jerks of the shoulders and arms. There is tonic abduction which results in progressive lifting of the arms during the seizure. Seizures last between 10 and 60 seconds and there may be a complete loss of awareness.

Eyelid myoclonia are absence seizures which are accompanied by brief repetitive myoclonic jerks of the eyelids with simultaneous upward deviation of the eyeballs and extension of the head. Seizures are typically brief and multiple seizures can occur on a daily basis. Awareness is mostly retained.

Absence seizures may occur in epilepsy syndromes including: Lennox-Gastaut Syndrome; Myoclonic Absence Epilepsy; Tuberous Sclerosis Complex; Dravet Syndrome; Doose Syndrome; CDKL5; Dup15q; Jeavons Syndrome; Myoclonic Absence Epilepsy; Neuronal ceroid lipofuscinoses (NCL) and brain abnormalities.

Epileptic syndromes often present with many different types of seizure and identifying the types of seizure that a patient is suffering from is important as many of the standard AED's are targeted to treat or are only effective against a given seizure type/sub-type.

The first line treatment for absence seizures usually comprises a broad spectrum AED, such as sodium valproate, lamotrigine or ethosuximide. A combination of these medicaments may be required in order to treat absence seizures.

Common AED defined by their mechanisms of action are described in the following tables:

TABLE 1

Examples of narrow spectrum AED

| Narrow-spectrum AED | Mechanism | Indication |
|---|---|---|
| Phenytoin | Sodium channel | Complex partial Tonic-clonic |
| Phenobarbital | GABA/Calcium channel | Partial seizures Tonic-clonic |
| Carbamazepine | Sodium channel | Partial seizures Tonic-clonic Mixed seizures |
| Oxcarbazepine | Sodium channel | Partial seizures Tonic-clonic Mixed seizures |
| Gabapentin | Calcium channel | Partial seizures Mixed seizures |
| Pregabalin | Calcium channel | Adjunct therapy for partial seizures with or without secondary generalisation |
| Lacosamide | Sodium channel | Adjunct therapy for partial seizures |
| Vigabatrin | GABA | Secondarily generalized tonic-clonic seizures Partial seizures Infantile spasms due to West syndrome |

TABLE 2

Examples of broad spectrum AED

| Broad-spectrum AED | Mechanism | Indication |
|---|---|---|
| Valproic acid | GABA/Sodium channel | First-line treatment for tonic-clonic seizures, absence seizures and myoclonic seizures Second-line treatment for partial seizures and infantile spasms. Intravenous use in status epilepticus |
| Lamotrigine | Sodium channel | Partial seizures Tonic-clonic Seizures associated with Lennox-Gastaut syndrome |
| Ethosuximide | Calcium channel | Absence seizures |
| Topiramate | GABA/Sodium channel | Seizures associated with Lennox-Gastaut syndrome |
| Zonisamide | GABA/Calcium/Sodium channel | Adjunctive therapy in adults with partial-onset seizures Infantile spasm Mixed seizure Lennox-Gastaut syndrome Myoclonic Generalised tonic-clonic seizure |
| Levetiracetam | Calcium channel | Partial seizures Adjunctive therapy for partial, myoclonic and tonic-clonic seizures |
| Clonazepam | GABA | Typical and atypical absences Infantile myoclonic Myoclonic seizures Akinetic seizures |
| Rufinamide | Sodium channel | Adjunctive treatment of partial seizures associated with Lennox-Gastaut syndrome |

TABLE 3

Examples of AED used specifically in childhood epilepsy

| AED | Mechanism | Indication |
|---|---|---|
| Clobazam | GABA | Adjunctive therapy in complex partial seizures Status epilepticus Myoclonic Myoclonic-absent Simple partial Complex partial Absence seizures Lennox-Gastaut syndrome |
| Stiripentol | GABA | Severe myoclonic epilepsy in infancy (Dravet syndrome) |

From these tables it can be seen that the three AED that are used as first line treatments for absence seizures, namely: sodium valproate, lamotrigine or ethosuximide are GABA/sodium channel, sodium channel and calcium channel drugs respectively.

It can also be seen from these tables that other AED are approved for use in absence seizures, these include clonazepam and clobazam, both of which work by a GABA mechanism.

Over the past forty years there have been a number of animal studies on the use of the non-psychoactive cannabinoid cannabidiol (CBD) to treat seizures. For example, Consroe et al., (1982) determined that CBD was able to prevent seizures in mice after administration of pro-convulsant drugs or an electric current.

Studies in epileptic adults have also occurred in the past forty years with CBD. Cunha et al. reported that administration of CBD to eight adult patients with generalized epilepsy resulted in a marked reduction of seizures in 4 of the patients (Cunha et al., 1980).

A study in 1978 provided 200 mg/day of pure CBD to four adult patients, two of the four patients became seizure free, whereas in the remainder seizure frequency was unchanged (Mechoulam and Carlini, 1978).

In contrast to the studies described above, an open label study reported that 200 mg/day of pure CBD was ineffective in controlling seizures in twelve institutionalized adult patients (Ames and Cridland, 1986).

Based on the fact that chronologically the last study to look at the effectiveness of CBD in patients with epilepsy proved that CBD was unable to control seizures, there would be no expectation that CBD might be useful as an anti-convulsant agent.

In the past forty years of research there have been over thirty drugs approved for the treatment of epilepsy none of which are cannabinoids. Indeed, there appears to have been a prejudice against cannabinoids, possibly due to the scheduled nature of these compounds and/or the fact that THC, which is a known psychoactive, has been ascribed as a pro-convulsant (Consroe et al., 1977).

A paper published recently suggested that cannabidiol-enriched *cannabis* may be efficacious in the treatment of epilepsy. Porter and Jacobson (2013) report on a parent survey conducted via a Facebook group which explored the use of *cannabis* which was enriched with CBD in children with treatment-resistant epilepsy. It was found that sixteen of the 19 parents surveyed reported an improvement in their child's epilepsy. The children surveyed for this paper were all taking *cannabis* that was purported to contain CBD in a high concentration although the amount of CBD present and the other constituents including THC were not known for many of the cases. Indeed, whilst CBD levels ranged from 0.5 to 28.6 mg/kg/day (in those extracts tested), THC levels as high as 0.8 mg/kg/day were reported.

Providing children with TRE with a *cannabis* extract that comprises THC, which has been described as a pro-convulsant (Consroe et al., 1977), at a potentially psychoactive dose of 0.8 mg/kg/day, is a concern and as such there is a need to determine whether CBD is in fact efficacious.

In November 2013 the company GW Pharmaceuticals made a press release to state that they were intending to treat Dravet Syndrome with CBD as it had received orphan drug designation.

To date there have been no controlled trials of CBD in children and young adults with intractable epilepsy.

BRIEF SUMMARY OF THE DISCLOSURE

In accordance with a first aspect of the present invention there is provided cannabidiol (CBD) for use in the treatment of epilepsy, wherein the epilepsy is characterised by absence seizures.

In one embodiment the epilepsy is a childhood epilepsy.

In one embodiment the absence seizures are myoclonic absence seizures.

Surprisingly, the CBD has been shown to be particularly effective in subjects with epilepsy which is treatment-resistant.

In a further embodiment the CBD is for use in combination with one or more concomitant anti-epileptic drugs (AED).

Preferably the absence seizures to be treated are in patients diagnosed with: Lennox-Gastaut Syndrome; Myoclonic Absence Epilepsy; Tuberous Sclerosis Complex; Dravet Syndrome; Doose Syndrome; Jeavons Syndrome; CDKL5; Dup15q; Neuronal ceroid lipofuscinoses (NCL) and brain abnormalities.

Most preferably the treatment-resistant epilepsy is one of: Lennox-Gastaut Syndrome; Dravet Syndrome and Myoclonic Absence Epilepsy.

In a further embodiment the CBD is present as a highly purified extract of *cannabis* which comprises at least 98% (w/w) CBD. Preferably the extract comprises less than 0.15% THC. More preferably the extract further comprises up to 1% CBDV.

In an alternative embodiment the CBD is present as a synthetic compound.

In a further embodiment of the invention the one or more AED is selected from the group consisting of: clobazam, clonazepam, clorazepate, desmethylclobazam, diazepam, ethosuximide, felbamate, gabapentin, ketogenic diet, lacosamide, lamotrigine, levetiracetam, lorazepam, midazolam, N-desmethylclobazam, nordiazepam, phenytoin, stiripentol, topiramate, trazodone, vagus nerve stimulation, valproic acid, vigabatrin, and zonisamide.

Preferably the one or more AED is selected from the group consisting of sodium valproate; lamotrigine; ethosuximide; clobazam and clonazepam.

Preferably the number of different anti-epileptic drugs that are used in combination with the CBD is reduced. Alternatively the dose of anti-epileptic drugs that are used in combination with the CBD is reduced.

There are many side effects associated with the commonly used AED which include dizziness, blurred vision, nausea, respiratory system depression, tiredness, headaches, and other motor side effects on the central nervous system. These side effects are particularly common as higher doses or combinations of numerous AED are used. As such there is a need for an alternative medication that is able to reduce the numbers of seizures whilst at the same time exhibiting a safe side effect profile.

Preferably the dose of CBD is greater than 5 mg/kg/day. Thus for a 15 kg patient a dose of greater than 75 mg of CBD per day would be provided. Doses greater than 5 mg/kg/day such as greater than 10/mg/kg/day, greater than 15 mg/kg/day, greater than 20 mg/kg/day and greater than 25 mg/kg/day are also envisaged to be effective.

Preferably the epilepsy is childhood epilepsy.

In accordance with a second aspect of the present invention there is provided a method of treating epilepsy comprising administering cannabidiol (CBD) to a subject, wherein the epilepsy is characterised by absence seizures.

Preferably the subject is a human, typically a patient that is suffering from epilepsy characterised by absence seizures.

In accordance with a third aspect of the present invention there is provided a composition for use in the treatment of epilepsy characterised by absence seizures comprising cannabidiol (CBD), a solvent, a co-solvent, a sweetener, and a flavouring.

Preferably the solvent is sesame oil, the co-solvent is ethanol, the sweetener is sucralose, the flavouring is strawberry flavour and the CBD is present at a concentration of between 25/mg/ml and 100 mg/ml, namely 50 mg/ml and 75 mg/ml.

More preferably the composition comprises cannabidiol (CBD) at a concentration of between 25 to 100 mg/ml, ethanol at a concentration of 79 mg/ml, sucralose at a concentration of 0.5 mg/ml, strawberry flavouring at a concentration of 0.2 mg/ml and sesame oil q.s. to 1.0 ml.

It is envisaged that the composition be administered as an oral liquid solution. Other modes of administration including solids, semi-solids, gels, sprays, aerosols, inhalers, vaporisers, enemas and suppositories are alternative administration forms. Such medicaments could be administered via the oral, buccal, sublingual, respiratory, nasal and distal rectum route.

BRIEF DESCRIPTION OF THE DRAWINGS

FIG. 1 shows the ILEA 2010 proposal for revised terminology for organization of seizures and epilepsies.

Definitions

Definitions of some of the terms used to describe the invention are detailed below:

The cannabinoids described in the present application are listed below along with their standard abbreviations.

TABLE 4

Cannabinoids and their abbreviations

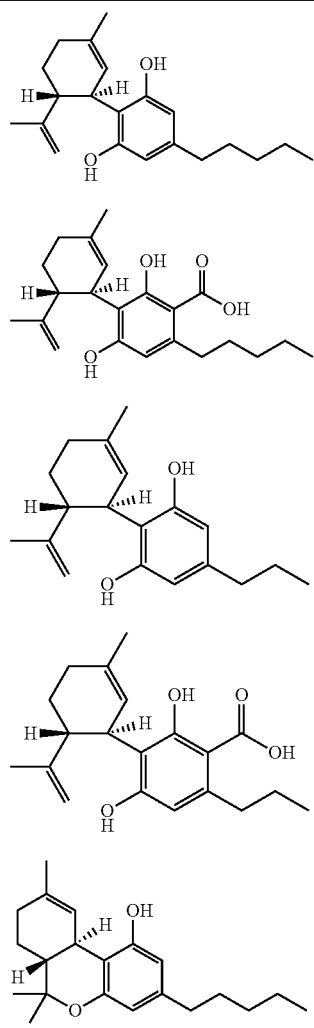

| CBD | Cannabidiol |
| CBDA | Cannabidiolic acid |
| CBDV | Cannabidivarin |
| CBDVA | Cannabidivarinic acid |
| THC | Tetrahydrocannabinol |

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the *cannabis* plant. The phytocannabinoids can be isolated from plants to produce a highly purified extract or can be reproduced synthetically.

"Highly purified cannabinoid extracts" are defined as cannabinoids that have been extracted from the *cannabis* plant and purified to the extent that other cannabinoids and non-cannabinoid components that are co-extracted with the cannabinoids have been substantially removed, such that the highly purified cannabinoid is greater than or equal to 98% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

"Treatment-resistant epilepsy" (TRE) or "intractable epilepsy" is defined as per the ILAE guidance of 2009 as epilepsy that is not adequately controlled by trials of one or more AED.

"Childhood epilepsy" refers to the many different syndromes and genetic mutations that can occur to cause epilepsy in childhood. Examples of some of these are as follows: Dravet Syndrome; Myoclonic-Absence Epilepsy; Lennox-Gastaut syndrome; Generalized Epilepsy of unknown origin; CDKL5 mutation; Aicardi syndrome; bilateral polymicrogyria; Dup15q; SNAP25; and febrile infection related epilepsy syndrome (FIRES); benign rolandic epilepsy; juvenile myoclonic epilepsy; infantile spasm (West syndrome); and Landau-Kleffner syndrome. The list above is non-exhaustive as many different childhood epilepsies exist.

"Absence Seizures" are defined as a generalised type of epileptic seizure which causes a loss of awareness often accompanied by myoclonic jerks.

"Myoclonic Absence Seizures" are defined as a sub-type of absence seizures which present with bilateral myoclonic jerks of the arms and shoulders.

"Mixed seizures" are defined as the existence of both generalised and focal seizures in the same patient.

The terms "50% responder" and "50% reduction in seizure" are both terms used in clinical studies. In the present application the terms define the percentage of subjects that experienced a greater than or equal to 50% reduction in the number of seizures during treatment with CBD in comparison to the number experienced during the baseline period before the CBD was administered.

DETAILED DESCRIPTION

Preparation of Highly Purified CBD Extract

The following describes the production of the highly-purified (>98% w/w) cannabidiol extract which has a known and constant composition which was used for the expanded access trials described in the Examples below.

In summary the drug substance used in the trials is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 98% CBD.

The *Cannabis sativa* L. plants are grown, harvested, and processed to produce a botanical extract (intermediate) and then purified by crystallization to yield the CBD (drug substance).

The plant starting material is referred to as Botanical Raw Material (BRM); the botanical extract is the intermediate; and the active pharmaceutical ingredient (API) is CBD, the drug substance.

Both the botanical starting material and the botanical extract are controlled by specifications. The drug substance specification is described in Table 5 below.

TABLE 5

CBD Specification

| Test | Test Method | Limits |
| --- | --- | --- |
| Appearance | Visual | Off-white/pale yellow crystals |
| Identification A | HPLC-UV | Retention time of major peak corresponds to certified CBD Reference Standard |
| Identification B | GC-FID/MS | Retention time and mass spectrum of major peak corresponds to certified CBD Reference Standard |
| Identification C | FT-IR | Conforms to reference spectrum for certified CBD Reference Standard |
| Identification D | Melting Point | 65-67° C. |
| Identification E | Specific Optical Rotation | Conforms with certified CBD Reference Standard; −110° to −140° (in 95% ethanol) |
| Total Purity | Calculation | ≥98.0% |
| Chromatographic Purity 1 | HPLC-UV | ≥98.0% |
| Chromatographic Purity 2 | GC-FID/MS | ≥98.0% |
| Other Cannabinoids: | HPLC-UV | |
| CBDA | | NMT 0.15% w/w |
| CBDV | | NMT 1.0% w/w |
| $\Delta^9$ THC | | NMT 0.15% w/w |
| CBD-C4 | | NMT 0.5% w/w |
| Residual Solvents: | GC | |
| Alkane | | NMT 0.5% w/w |
| Ethanol | | NMT 0.5% w/w |
| Residual Water | Karl Fischer | NMT 1.0% w/w |

NMT—Not more than

The purity of the CBD drug substance achieved is greater than 98%. The other cannabinoids which may occur in the extract are: CBDA, CBDV, CBD-C4 and THC.

Distinct chemotypes of *Cannabis sativa* L. plant have been produced to maximize the output of the specific chemical constituents, the cannabinoids. One type of plant produces predominantly CBD. Only the (−)-trans isomer occurs naturally. Furthermore during purification the stereochemistry of CBD is not affected.

Production of the Intermediate

An overview of the steps to produce a botanical extract, the intermediate, are as follows:
1. Growing
2. Decarboxylation
3. Extraction No. 1-using liquid $CO_2$
4. Extraction No. 2-'winterization' using ethanol
5. Filtration
6. Evaporation High CBD chemovars were grown, harvested and dried and stored in a dry room until required. The botanical raw material (BRM) was finely chopped using an Apex mill fitted with a 1 mm screen. The milled BRM was stored in a freezer for up to 3 months prior to extraction.

Decarboxylation of CBDA to CBD was carried out using a large Heraeus tray oven. The decarboxylation batch size in the Heraeus is approximately 15 Kg. Trays were placed in the oven and heated to 105° C.; the BRM took 96.25 minutes to reach 105° C. Held at 105° C. for 15 Minutes. Oven then set to 150° C.; the BRM took 75.7 minutes to reach 150° C.; BRM held at 150° C. for 130 Minutes. Total time in the oven was 380 Minutes, including 45 minutes cooling and 15 Minutes venting.

Extraction No 1 was performed using liquid $CO_2$ at 60 bar/10° C. to produce botanical drug substance (BDS).

The crude CBD BDS was winterised in Extraction No 2 under standard conditions (2 volumes of ethanol at minus 20° C. for around 50 hours). The precipitated waxes were removed by filtration and the solvent evaporated using the rotary evaporator (water bath up to 60° C.) to yield the BDS, which was then used for crystallisation to produce the test material.

Production of the Drug Substance

The manufacturing steps to produce the drug substance from the intermediate botanical extract are as follows:
1. Crystallization using C5-C12 straight chain or branched alkane
2. Filtration
3. Optional recrystallization from C5-C12 straight chain or branched alkane
4. Vacuum drying Intermediate botanical extract (12 kg) produced using the methodology above was dispersed in C5-C12 straight chain or branched alkane (9000 ml, 0.75 vols) in a 30 litre stainless steel vessel.

The mixture was manually agitated to break up any lumps and the sealed container then placed in a freezer for approximately 48 hours.

The crystals were isolated by vacuum filtration, washed with aliquots of cold C5-C12 straight chain or branched alkane (total 12000 ml), and dried under a vacuum of <10 mb at a temperature of 60° C. until dry before submitting the drug substance for analysis.

The dried product was stored in a freezer at minus 20° C. in a pharmaceutical grade stainless steel container, with FDA food grade approved silicone seal and clamps.

Production of the Drug Product

The drug product is presented as an oral solution. The oral solution presentation contains 25 mg/ml or 100 mg/ml CBD, with the excipients sesame oil, ethanol, sweetener and flavouring. Two product strengths are available to allow dose titration across a wide dose range.

The 25 mg/ml solution is appropriate at lower doses and the 100 mg/ml solution at higher doses.

The drug product formulation is as described in Table 6 below:

TABLE 6

Drug Product specification

| Component | Qualitative Composition | Function | Reference to Quality Standard |
| --- | --- | --- | --- |
| Cannabidiol (CBD) | 25 mg/ml or 100 mg/ml | Active | In-house |
| Anhydrous ethanol | 79.0 mg/ml* | Excipient | Ph. Eur. |

TABLE 6-continued

Drug Product specification

| Component | Qualitative Composition | Function | Reference to Quality Standard |
|---|---|---|---|
| Sucralose | 0.5 mg/ml | Sweetener | In-house |
| Strawberry flavouring | 0.2 mg/ml | Flavouring | In-house |
| Sesame oil | q.s to 1.0 ml | Excipient | Ph. Eur. |

The drug substance, CBD is insoluble in water. Sesame oil was selected as an excipient to solubilize the drug substance.

A sweetener and fruit flavouring are required to improve palatability of the sesame oil solution.

Ethanol was required to solubilize the sweetener and the flavouring.

The composition can be substantially equivalent, by which is meant the functional ingredients can vary from the qualitative composition specified in Table 6 by an amount of up to 10%.

Example 1 below describes the use of a highly purified *cannabis* extract comprising cannabidiol (CBD). Cannabidiol is the most abundant non-psychoactive cannabinoid in the selected chemovar. Previous studies in animals have demonstrated that CBD has anticonvulsant efficacy in multiple species and models.

Example 1 describes data produced in an expanded access treatment program in children with TRE.

Example 1

Efficacy of Cannabidiol Reducing Absence Seizures in Children and Young Adults with Intractable Epilepsy Materials and Methods Of 137 children and young adults with severe, childhood onset treatment-resistant epilepsy (TRE), forty-two suffered from epilepsy that was characterised by absence seizures. These subjects were tested with a highly purified extract of cannabidiol (CBD) obtained from a *cannabis* plant. All subjects presented with absence type seizures, often in addition to other generalised and/or focal seizures. The participants in the study were part of an expanded access compassionate use program for CBD.

The epileptic syndromes that these patients suffered from were as follows: Lennox-Gastaut Syndrome; Myoclonic Absence Epilepsy; Tuberous Sclerosis Complex; Dravet Syndrome; Doose Syndrome; Jeavons Syndrome; CDKL5; Dup15q; Neuronal ceroid lipofuscinoses (NCL) and brain abnormalities.

Seizure types experienced by these patients included: tonic, clonic, tonic-clonic, myoclonic, atonic, absence, myoclonic-absence, focal seizures without impairment, focal seizures with impairment and focal seizures evolving to bilateral convulsive seizures.

All patients entered a baseline period of 4 weeks when parents/caregivers kept prospective seizure diaries, noting all countable seizure types.

The patients then received a highly purified CBD extract (greater than 98% CBD w/w) in sesame oil, of known and constant composition, at a dose of 5 mg/kg/day in addition to their baseline anti-epileptic drug (AED) regimen.

The daily dose was gradually increased by 2 to 5 mg/kg increments until intolerance occurred or a maximum dose of 25 mg/kg/day was achieved.

Patients were seen at regular intervals of 2-4 weeks. Laboratory testing for hematologic, liver, kidney function, and concomitant AED levels was performed at baseline, and after every 4 weeks of CBD therapy.

The patients on the study were all taking at least one concomitant AED. These included clobazam, clonazepam, clorazepate, desmethylclobazam, diazepam, ethosuximide, felbamate, gabapentin, ketogenic diet, lacosamide, lamotrigine, levetiracetam, lorazepam, midazolam, N-desmethylclobazam, nordiazepam, phenytoin, stiripentol, topiramate, trazodone, vagus nerve stimulation, valproic acid, vigabatrin, and zonisamide.

Results

Of the 42 children and young adult patients who received treatment with CBD, there were 28 patients who received treatment for at least 12 weeks of treatment all of whom suffered from absence type seizures.

A summary of the 50% responders, based on 12 weeks of treatment are summarized in Table 7 below.

TABLE 7

Summary of 50% responders after 12 weeks of treatment

| | Absence seizures (n = 28) | Total seizures (n = 137) |
|---|---|---|
| >50% reduction in seizures | 64% (n = 18) | 46% (n = 63) |
| <50% reduction in seizures | 36% (n = 10) | 54% (n = 74) |

Table 7 shows that after 3 months of therapy, a remarkable 64% of patients had an equal to or greater than >50% reduction in absence seizures, these data infer that the CBD is very effective at reducing this type of seizure.

Conclusions

These data indicate that CBD significantly reduces the number of absence type seizures in a high proportion of patients that do not respond well to existing AED.

It was surprising that in this group of patients which are treatment-resistant such a high number were able to gain an effect. The fact that nearly two thirds of the patients (64%) benefitted from at least a fifty percent reduction in the number of absence seizures that they suffered from was remarkable.

Example 2

Efficacy of Cannabidiol Reducing Myoclonic Absence Seizures in Children and Young Adults with Intractable Epilepsy Materials and Methods Of 137 children and young adults with severe, childhood onset treatment-resistant epilepsy (TRE), ten suffered from epilepsy that was characterised by myoclonic absence seizures. These subjects were tested with a highly purified extract of cannabidiol (CBD) obtained from a *cannabis* plant. All subjects presented with myoclonic absence type seizures, often in addition to other generalised and/or focal seizures. The participants in the study were part of an expanded access compassionate use program for CBD.

The epileptic syndromes that these patients suffered from were as follows: Myoclonic Absence Epilepsy; Doose Syndrome; and epilepsy of unknown cause.

All patients entered a baseline period of 4 weeks when parents/caregivers kept prospective seizure diaries, noting all countable seizure types.

The patients then received a highly purified CBD extract (greater than 98% CBD w/w) in sesame oil, of known and constant composition, at a dose of 5 mg/kg/day in addition to their baseline anti-epileptic drug (AED) regimen.

The daily dose was gradually increased by 2 to 5 mg/kg increments until intolerance occurred or a maximum dose of 25 mg/kg/day was achieved.

Patients were seen at regular intervals of 2-4 weeks. Laboratory testing for hematologic, liver, kidney function, and concomitant AED levels was performed at baseline, and after every 4 weeks of CBD therapy.

The patients on the study were all taking at least one concomitant AED. These included clobazam, clonazepam, clorazepate, diazepam, ethosuximide, ketogenic diet, lacosamide, lamotrigine, levetiracetam, lorazepam, midazolam, and valproic acid.

Results

Of the 10 children and young adult patients who received treatment with CBD, there were 8 patients who received treatment for at least 12 weeks of treatment all of whom suffered from myoclonic absence type seizures.

A summary of the 50% responders, based on 12 weeks of treatment are summarized in Table 8 below.

TABLE 8

Summary of 50% responders after 12 weeks of treatment

| | Myoclonic absence seizures (n = 10) | Total seizures (n = 137) |
|---|---|---|
| >50% reduction in seizures | 75% (n = 6) | 46% (n = 63) |
| <50% reduction in seizures | 25% (n = 2) | 54% (n = 74) |

Table 8 shows that after 3 months of therapy, a remarkable 75% of patients had an equal to or greater than >50% reduction in absence seizures, these data infer that the CBD is very effective at reducing this type of seizure.

Conclusions

These data indicate that CBD significantly reduces the number of myoclonic absence seizures in a high proportion of patients that do not respond well to existing AED.

It was surprising that in this group of patients which are treatment-resistant such a high number were able to gain an effect. The fact that nearly three quarters of the patients (75%) benefitted from at least a fifty percent reduction in the number of myoclonic absence seizures that they suffered from was remarkable.

REFERENCES

Ames F R and Cridland S (1986). "Anticonvulsant effects of cannabidiol." S Afr Med J 69:14.

Consroe P, Martin P, Eisenstein D. (1977). "Anticonvulsant drug antagonism of delta-9-tetrahydrocannabinol induced seizures in rabbits." Res Commun Chem Pathol Pharmacol. 16:1-13

Consroe P, Benedicto M A, Leite J R, Carlini E A, Mechoulam R. (1982). "Effects of cannabidiol on behavioural seizures caused by convulsant drugs or current in mice." Eur J Pharmaco. 83: 293-8

Cunha J M, Carlini E A, Pereira A E, Ramos O L, Pimental C, Gagliardi R et al. (1980). "Chronic administration of cannabidiol to healthy volunteers and epileptic patient." Pharmacology. 21:175-85

Dravet C. The core Dravet syndrome phenotype. Epilepsia. 2011 April; 52 Suppl 2:3-9.

Eadie, M J (December 2012). "Shortcomings in the current treatment of epilepsy." Expert *Review of Neurotherapeutics* 12 (12): 1419-27.

Kwan P, Arzimanoglou A, Berg A T, Brodie M J, Hauser W A, Mathern G, Moshé S L, Perucca E, Wiebe S, French J. (2009) "Definition of drug resistant epilepsy: Consensus proposal by the ad hoc Task Force of the ILAE Commission on Therapeutic Strategies." *Epilepsia*.

Mechoulam R and Carlini E A (1978). "Toward drugs derived from *cannabis*." Die naturwissenschaften 65:174-9.

Porter B E, Jacobson C (December 2013). "Report of a parent survey of cannabidiol-enriched *cannabis* use in paediatric treatment resistant epilepsy" Epilepsy Behaviour. 29(3) 574-7

Thurman, D J; Beghi, E; Begley, C E; Berg, A T; Buchhalter, J R; Ding, D; Hesdorffer, D C; Hauser, W A; Kazis, L; Kobau, R; Kroner, B; Labiner, D; Liow, K; Logroscino, G; Medina, M T; Newton, C R; Parko, K; Paschal, A; Preux, P M; Sander, J W; Selassie, A; Theodore, W; Tomson, T; Wiebe, S; ILAE Commission on, Epidemiology (September 2011). "Standards for epidemiologic studies and surveillance of epilepsy." *Epilepsia*. 52 Suppl 7: 2-26

The invention claimed is:

1. A method of treating absence seizures in a subject diagnosed with an epilepsy selected from Lennox-Gastaut Syndrome, Myoclonic Absence Epilepsy, and Dravet Syndrome, comprising administering cannabidiol (CBD) to a subject, wherein the CBD is administered at a dose of from about 10 mg/kg/day to about 20 mg/kg/day, wherein the CBD has a purity of at least 98% (w/w) CBD and comprises no more than 0.15% (w/w) Δ9-tetrahydrocannabidiol.

2. The method according to claim 1, wherein the absence seizures are myoclonic absence seizures.

3. The method according to claim 1, wherein the epilepsy is treatment-resistant epilepsy (TRE).

4. The method according to claim 1, wherein the CBD is administered in combination with one or more concomitant anti-epileptic drugs (AED).

5. The method according to claim 1, wherein the subject is diagnosed with Lennox-Gastaut Syndrome.

6. The method according to claim 1, wherein the subject is diagnosed with Dravet Syndrome.

7. The method according to claim 1, wherein the subject is diagnosed with Myoclonic Absence Epilepsy.

8. The method according to claim 1, wherein the CBD is a highly purified extract of *cannabis*.

9. The method according to claim 8, wherein the extract further comprises up to 1% CBDV.

10. The method according to claim 1, wherein the CBD is present as a synthetic compound.

11. The method according to claim 4, wherein the one or more concomitant AED is selected from the group consisting of: sodium valproate; lamotrigine; clobazam; and clonazepam.

12. The method according to claim 4, wherein the number of different concomitant anti-epileptic drugs that are used in combination with the CBD is reduced.

13. The method according to claim 4, wherein the dose of the concomitant AED that is used in combination with the CBD is reduced.

14. A method of treating absence seizures in a subject diagnosed with Lennox-Gastaut Syndrome, comprising administering cannabidiol (CBD) to a subject, wherein the CBD is administered at a dose of from about 5 mg/kg/day to about 25 mg/kg/day, wherein the CBD has a purity of at least 98% (w/w) CBD and comprises no more than 0.15% (w/w) Δ9-tetrahydrocannabidiol.

15. A method of treating absence seizures in a subject diagnosed with Dravet Syndrome, comprising administering cannabidiol (CBD) to a subject, wherein the CBD is administered at a dose of from about 5 mg/kg/day to about 25 mg/kg/day, and wherein the CBD has a purity of at least 98% (w/w) CBD and comprises no more than 0.15% (w/w) Δ9-tetrahydrocannabidiol.

16. The method of claim 14, wherein the dose of CBD is 10 mg/kg/day.

17. The method of claim 14, wherein the dose of CBD is 20 mg/kg/day.

18. The method of claim 15, wherein the dose of CBD is 10 mg/kg/day.

19. The method of claim 15, wherein the dose of CBD is 20 mg/kg/day.

20. The method of claim 1, wherein the dose of CBD is 10 mg/kg/day.

21. The method of claim 1, wherein the dose of CBD is 20 mg/kg/day.

\* \* \* \* \*